US00RE49500E

(19) United States
(12) Reissued Patent
Martinez Botella et al.

(10) Patent Number: US RE49,500 E
(45) **Date of Reissued Patent: *Apr. 25, 2023**

(54) PYRROLE INHIBITORS OF ERK PROTEIN KINASE, SYNTHESIS THEREOF AND INTERMEDIATES THERETO

(71) Applicant: VERTEX PHARMACEUTICALS INCORPORATED, Boston, MA (US)

(72) Inventors: Gabriel Martinez Botella, Wayland, MA (US); Michael Hale, Bedford, MA (US); Francois Maltais, Tewksbury, MA (US); Judith Straub, Ardmore, PA (US); Qing Tang, Acton, MA (US)

(73) Assignee: VERTEX PHARMACEUTICALS INCORPORATED, Boston, MA (US)

( * ) Notice: This patent is subject to a terminal disclaimer.

(21) Appl. No.: 17/071,566

(22) Filed: Oct. 15, 2020

Related U.S. Patent Documents

Reissue of:
(64) Patent No.: 7,354,939
Issued: Apr. 8, 2008
Appl. No.: 11/128,870
Filed: May 13, 2005

U.S. Applications:
(63) Continuation of application No. 16/363,905, filed on Mar. 25, 2019, now Pat. No. Re. 48,266, which is an application for the reissue of Pat. No. 7,354,939, and a continuation of application No. 15/195,021, filed on Jun. 28, 2016, now Pat. No. Re. 47,318, which is a continuation of application No. 14/544,396, filed on Aug. 23, 2013, now Pat. No. Re. 46,097, which is an application for the reissue of Pat. No. 7,354,939.

(60) Provisional application No. 60/571,309, filed on May 14, 2004.

(51) Int. Cl.
*C07F 9/6558* (2006.01)
*C07D 401/04* (2006.01)

(52) U.S. Cl.
CPC ..... *C07F 9/65583* (2013.01); *C07D 401/04* (2013.01)

(58) Field of Classification Search
CPC ..... C07F 9/65583; C07D 401/04; A61P 1/04; A61P 1/16; A61P 1/18; A61P 9/00; A61P 9/10; A61P 15/00; A61P 17/00; A61P 19/08; A61P 25/00; A61P 29/00; A61P 31/12; A61P 35/00; A61P 35/02; A61P 37/00; A61P 37/02; A61P 37/04; A61P 37/06; A61P 43/00
See application file for complete search history.

(56) References Cited

U.S. PATENT DOCUMENTS

| | | | | |
|---|---|---|---|---|
| 5,472,966 | A | 12/1995 | Sloan et al. | 514/255 |
| 5,565,413 | A | 10/1996 | Kanne | 504/254 |
| 6,743,791 | B2 | 6/2004 | Cao et al. | |
| 7,253,187 | B2 | 8/2007 | Cao et al. | |
| RE46,097 | E * | 8/2016 | Botella | A61P 25/00 |
| RE47,318 | E * | 3/2019 | Botella | A61P 35/00 |
| RE48,266 | E * | 10/2020 | Botella | A61P 1/16 |
| 2004/0220200 | A1* | 11/2004 | Maltais et al. | 514/269 |
| 2004/0229875 | A1 | 11/2004 | Cao et al. | 514/242 |

FOREIGN PATENT DOCUMENTS

| | | | |
|---|---|---|---|
| EP | 1 188 755 | | 3/2002 |
| EP | 1 188 755 | A1 | 3/2002 |
| WO | 2002064586 | | 8/2002 |
| WO | WO 02/064586 | A2 | 8/2002 |
| WO | 2003091246 | | 11/2003 |
| WO | WO 03/091246 | A1 | 11/2003 |
| WO | 2004005283 | | 1/2004 |
| WO | 2004009562 | | 1/2004 |
| WO | WO 2004/005283 | A1 | 1/2004 |
| WO | WO 2004/009562 | A1 | 1/2004 |
| WO | 2004013125 | | 2/2004 |
| WO | 2004016597 | | 2/2004 |
| WO | WO 2004/013125 | A1 | 2/2004 |
| WO | WO 2004/016597 | A2 | 2/2004 |
| WO | 2004083203 | | 9/2004 |
| WO | WO 2004/083203 | A1 | 9/2004 |

OTHER PUBLICATIONS

International Search Report dated Aug. 10, 2004, in International Patent Application No. PCT/US2005/016902, filed May 13, 2005, by Vertex Pharmaceuticals, Inc.
Blanchard et al. "Hetarynic Synthesis and Chemical Transformation of Dihydrodipyridopyrazines," Tetrahedron 58(18):3513-3524 (2002).

* cited by examiner

*Primary Examiner* — Jerry D Johnson
(74) *Attorney, Agent, or Firm* — Bryan Cave Leighton Paisner LLP

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

8 Claims, No Drawings

PYRROLE INHIBITORS OF ERK PROTEIN KINASE, SYNTHESIS THEREOF AND INTERMEDIATES THERETO

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

[This application claims priority to U.S. Provisional Patent Application 60/571,309 filed May 14, 2004, the entire contents of which are hereby incorporated by reference.] *Notice: More than one reissue application has been filed for the reissue of U.S. Pat. No. 7,354,939. The reissue applications are Reissue application Ser. No. 16/363,905, now U.S. Pat. No. RE48,266, Reissue application Ser. No. 15/195,021, now U.S. Pat. No. RE47,318, Reissue application Ser. No. 14/544,396, now U.S. Pat. No. RE46,097, and the present application filed herewith. This application is a continuation reissue application of U.S. patent application Ser. No. 16/363,905, filed Mar. 25, 2019, now U.S. Pat. No. RE48, 266, which is a continuation reissue application of U.S. patent application Ser. No. 15/195,021, filed Jun. 28, 2016, now U.S. Pat. No. RE47,318, which is a continuation reissue application of U.S. application Ser. No. 14/544,396, filed Aug. 23, 2013, now U.S. Pat. No. RE46,097, which is an application for reissue of U.S. Pat. No. 7,354,939, issued on Apr. 8, 2008, from U.S. patent application Ser. No. 11/128, 870, filed on May 13, 2005, which claims the benefit of priority of U.S. Provisional Application No. 60/571,309, filed on May 14, 2004, all of which are incorporated herein by reference in their entirety.*

TECHNICAL FIELD OF INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J., 9:576-596 (1995); Knighton et al., Science, 253:407-414 (1991); Hiles et al., Cell, 70:419-429 (1992); Kunz et al., Cell, 73:585-596 (1993); Garcia-Bustos et al., EMBO J., 13:2352-2361 (1994)).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents. However, considering the lack of currently available treatment options for the majority of the conditions associated with protein kinases, there is still a great need for new therapeutic agents that inhibit these protein targets.

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

ERK2 is a widely distributed protein kinase that achieves maximum activity when both Thr183 and Tyr185 are phosphorylated by the upstream MAP kinase kinase, MEK1 (Anderson et al., 1990, Nature 343, 651; Crews et al., 1992, Science 258, 478). Upon activation, ERK2 phosphorylates many regulatory proteins, including the protein kinases Rsk90 (Bjorbaek et al., 1995, J. Biol. Chem. 270, 18848) and MAPKAP2 (Rouse et al., 1994, Cell 78, 1027), and transcription factors such as ATF2 (Raingeaud et al., 1996, Mol. Cell Biol. 16, 1247), Elk-1 (Raingeaud et al. 1996), c-Fos (Chen et al., 1993 Proc. Natl. Acad. Sci. USA 90, 10952), and c-Myc (Oliver et al., 1995, Proc. Soc. Exp. Biol. Med. 210, 162). ERK2 is also a downstream target of the Ras/Raf dependent pathways (Moodie et al., 1993, Science 260, 1658) and relays the signals from these potentially oncogenic proteins. ERK2 has been shown to play a role in the negative growth control of breast cancer cells (Frey and Mulder, 1997, Cancer Res. 57, 628) and hyperexpression of ERK2 in human breast cancer has been reported (Sivaraman et al., 1997, J. Clin. Invest. 99, 1478). Activated ERK2 has also been implicated in the proliferation of endothelin-stimulated airway smooth muscle cells, suggesting a role for this kinase in asthma (Whelchel et al., 1997, Am. J. Respir. Cell Mol. Biol. 16, 589).

Overexpression of receptor tyrosine kinases such as EGFR and ErbB2 (Arteaga C L, 2002, Semin Oncol. 29, 3-9; Eccles S A, 2001, J Mammary Gland Biol Neoplasia 6:393-406; Mendelsohn J & Baselga J, 2000, Oncogene 19, 6550-65), as well as activating mutations in the Ras GTPase proteins (Nottage M & Siu L L, 2002, Curr Pharm Des 8, 2231-42; Adjei A A, 2001, J Natl Cancer Inst 93, 1062-74) or B-Raf mutants (Davies H. et al., 2002, Nature 417, 949-54; Brose et al., 2002, Cancer Res 62, 6997-7000) are major contributors to human cancer. These genetic alterations are correlated with poor clinical prognosis and result in activation of the Raf-1/2/3-MEK1/2-ERK1/2 signal transduction cascade in a broad panel of human tumors. Activated ERK (i.e. ERK1 and/or ERK2) is a central signaling molecule that has been associated with the control of proliferation, differentiation, anchorage-independent cell survival, and angiogenesis, contributing to a number of processes that are important for the formation and progression of malignant tumors. These data suggest that an ERK1/2 inhibitor will exert pleiotropic activity, including proapoptotic, anti-proliferative, anti-metastatic and anti-angiogenic effects, and offer a therapeutic opportunity against a very broad panel of human tumors.

There is a growing body of evidence that implicates constitutive activation of the ERK MAPK pathway in the oncogenic behavior of select cancers. Activating mutations of Ras are found in ~30% of all cancers, with some, such as pancreatic (90%) and colon (50%) cancer, harboring particularly high mutation rates (ref). Ras mutations have also been identified in 9-15% of melanomas, but B-Raf somatic missense mutations conferring constitutive activation are more frequent and found in 60-66% malignant melanomas. Activating mutations of Ras, Raf and MEK are able to oncogenically transform fibroblasts in vitro, and Ras or Raf mutations in conjunction with the loss of a tumor suppressor gene (e.g. p16INK4A) can cause spontaneous tumor development in vivo. Increased ERK activity has been demonstrated in these models and has also been widely reported in appropriate human tumors. In melanoma, high basal ERK activity resulting from either B-Raf or N-Ras mutations or autocrine growth factor activation is well documented and has been associated with rapid tumor growth, increased cell survival and resistance to apoptosis. Additionally, ERK activation is considered a major driving force behind the highly metastatic behavior of melanoma associated with increased expression of both extracellular matrix degrading proteases and invasion-promoting integrins as well as the downregulation of E-cadherin adhesion molecules that normally mediate keratinocyte interactions to control melanocyte growth. These data taken together, indicate ERK as promising therapeutic target for the treatment of melanoma, a currently untreatable disease.

SUMMARY OF THE INVENTION

It has now been found that compounds of this invention, and pharmaceutically acceptable compositions thereof, are effective as inhibitors of ERK protein kinase. These compounds have the general formula I:

I

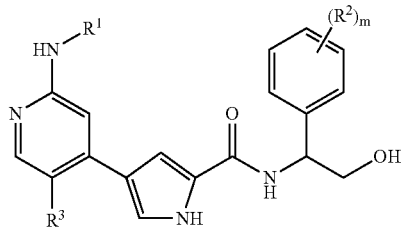

or a pharmaceutically acceptable salt thereof, wherein m, $R^1$, $R^2$, and $R^3$ are as defined below.

These compounds, and pharmaceutically acceptable compositions thereof, are useful for treating or lessening the severity of a variety of disorders, especially proliferative disorders such as cancer.

The compounds provided by this invention are also useful for the study of kinases in biological and pathological phenomena and the study of intracellular signal transduction pathways mediated by such kinases, and the comparative evaluation of new kinase inhibitors.

DETAILED DESCRIPTION OF CERTAIN EMBODIMENTS OF THE INVENTION

1. General Description of Compounds of the Invention:

The present invention relates to a compound of formula I:

I

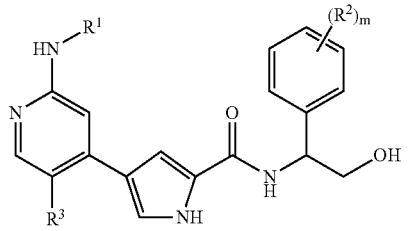

or a pharmaceutically acceptable salt thereof, wherein:

$R^1$ is a $C_{1-6}$ aliphatic group, wherein $R^1$ is optionally substituted with up to 2 groups independently selected from —OR or —$C_{1-3}$ haloalkyl;

each R is independently hydrogen or $C_{1-4}$ aliphatic;

each $R^2$ is independently R, fluoro, or chloro;

m is 0, 1, or 2; and $R^3$ is hydrogen, $C_{1-3}$ aliphatic, fluoro, or chloro.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "prodrug" refers to a derivative of a parent drug molecule that requires transformation within the body in order to release the active drug, and that has improved physical and/or delivery properties over the parent drug molecule. Prodrugs are designed to enhance pharmaceutically and/or pharmacokinetically based properties associated with the parent drug molecule. The advantage of a prodrug lies in its physical properties, such as enhanced water solubility for parenteral administration at physiological pH compared to the parent drug, or it enhances absorption from the digestive tract, or it may enhance drug stability for long-term storage. In recent years several types of bioreversible derivatives have been exploited for utilization in designing prodrugs. Using esters as a prodrug type for drugs containing carboxyl or hydroxyl function is known in the art as described, for example, in "The Organic Chemistry of Drug Design and Drug Interaction" Richard Silverman, published by Academic Press (1992).

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In certain embodiments, aliphatic groups contain 1-6 aliphatic carbon atoms, and in yet other embodiments, aliphatic groups contain 1-4 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; $R^o$; $OR^o$; $SR^o$; 1,2-methylene-dioxy; 1,2-ethylenedioxy; phenyl (Ph) optionally substituted with $R^o$; —O(Ph) optionally substituted with $R^o$; $(CH_2)_{1-2}$(Ph), optionally substituted with $R^o$; CH═CH(Ph), optionally substituted with $R^o$; $NO_2$; CN; $N(R^o)_2$; $NR^oC(O)R^o$; $NR^oC(O)N(R^o)_2$; $NR^oCO_2R^o$; —$NR^oNR^oC(O)R^o$; $NR^oNR^oC(O)N(R^o)_2$; $NR^oNR^oCO_2R^o$; $C(O)C(O)R^o$; $C(O)CH_2C(O)R^o$; $CO_2R^o$; $C(O)R^o$; $C(O)N(R^o)_2$; $OC(O)N(R^o)_2$; $S(O)_2R^o$; $SO_2N(R^o)_2$; $S(O)R^o$; $NR^oSO_2N(R^o)_2$; $NR^oSO_2R^o$; $C(=S)N(R^o)_2$; C(═NH)—$N(R^o)_2$; or $(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, O(Ph), or $CH_2$(Ph), or, notwithstanding the definition above, two independent occurrences of $R^o$, on the same substituent or different substituents, taken together with the atom(s) to which each $R^o$ group is bound, form a 3-8 membered cycloalkyl, heterocyclyl, aryl, or heteroaryl ring having 0-4 heteroatoms independently selected from nitrogen, oxygen, or sulfur. Optional substituents on the aliphatic group of $R^o$ are selected from $NH_2$, $NH(C_{1-4}$aliphatic), $N(C_{1-4}$ aliphatic$)_2$, halogen, $C_{1-4}$aliphatic, OH, $O(C_{1-4}$aliphatic), $NO_2$, CN, $CO_2H$, $CO_2(C_{1-4}$aliphatic), O(halo$C_{1-4}$ aliphatic), or halo$C_{1-4}$ aliphatic, wherein each of the foregoing $C_{1-4}$aliphatic groups of $R^o$ is unsubstituted.

An aliphatic or heteroaliphatic group or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═$NN(R^*)_2$, ═NNHC(O)R*, ═$NNHCO_2$(alkyl), ═$NNHSO_2$(alkyl), or ═NR, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from $R^+$, $N(R^+)_2$, $C(O)R^+$, $CO_2R^+$, $C(O)C(O)R^+$, $C(O)CH_2C(O)R^+$, $SO_2R^+$, $SO_2N(R^+)_2$, $C(=S)N(R^+)_2$, C(═NH)—$N(R^+)_2$, or $NR^+SO_2R^+$; wherein $R^+$ is hydrogen, an optionally substituted $C_{1-6}$ aliphatic, optionally substituted phenyl, optionally substituted O(Ph), optionally substituted $CH_2$(Ph), optionally substituted $(CH_2)_{1-2}$(Ph); optionally substituted CH═CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-4 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of $R^+$ is unsubstituted.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unlessotherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds:

According to one embodiment, the present invention relates to a compound of formula I wherein said compound is of formula Ia or Ib:

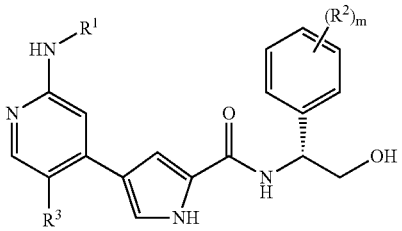

Ia

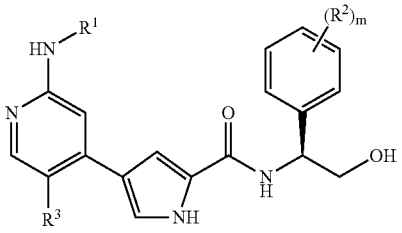

Ib or a pharmaceutically acceptable salt thereof, wherein each m, $R^1$, $R^2$, and $R^3$ group is as defined above.

According to certain embodiments, the $R^1$ moiety of any of formulae I, Ia, and Ib, is $C_{1-4}$ aliphatic optionally substituted with —OR or —$C_{1-3}$ haloalkyl. In certain embodiments, the $R^1$ moiety of any of formulae I, Ia, and Ib is $C_{1-4}$ aliphatic optionally substituted with —OH, —$CH_2F$, —$CHF_2$, or —$CF_3$. In other embodiments, the $R^1$ moiety of any of formulae I, Ia, and Ib is $C_{1-4}$ aliphatic optionally substituted with —OH. In yet other embodiments, $R^1$ is unsubstituted.

According to another embodiment, the $R^1$ moiety of any of formulae I, Ia, and Ib is isopropyl, 2-butyl, cyclopropyl, or ethyl, wherein each moiety is optionally substituted with —OH, —$CHF_2$, —$CH_2F$, or —$CF_3$. In certain embodiments, the $R^1$ moiety of any of formulae I, Ia, and Ib is optionally substituted with —OH or —$CF_3$.

Another aspect of the present invention relates to a compound of any of formulae I, Ia, and Ib wherein $R^2$ is hydrogen, $C_{1-3}$ aliphatic, or chloro. According to yet another aspect, the present invention relates to a compound of any of formulae I, Ia, and Ib wherein $R^2$ is chloro.

In certain embodiments, m is 1.

In other embodiments, the $R^3$ moiety of any of formulae I, Ia, and Ib is hydrogen, methyl, or chloro.

Representative compounds of formula I are set forth in Table 1 below.

TABLE 1

| Examples of Compounds of Formula I: | |
|---|---|
| 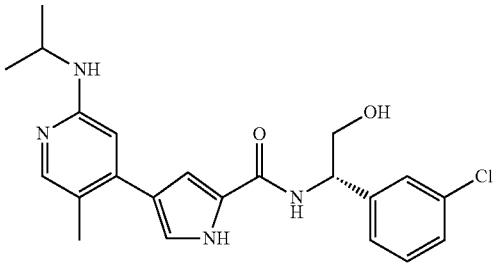 | I-1 |
| 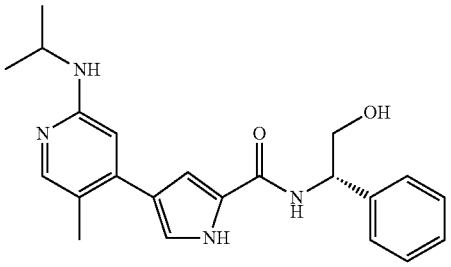 | I-2 |
| 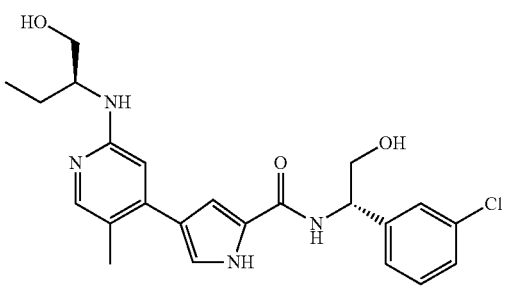 | I-3 |

TABLE 1-continued
Examples of Compounds of Formula I:
I-4
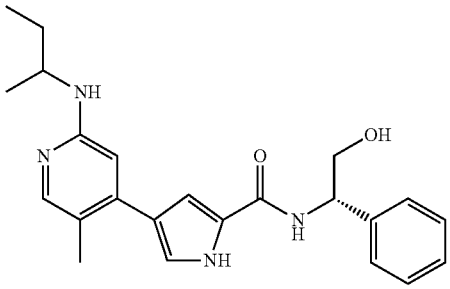
I-5
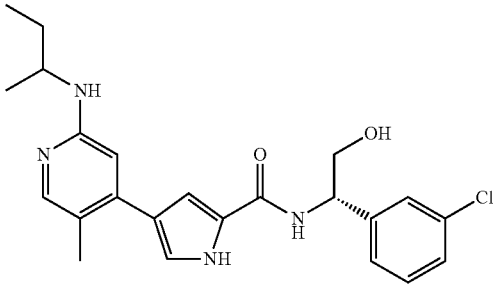
I-6
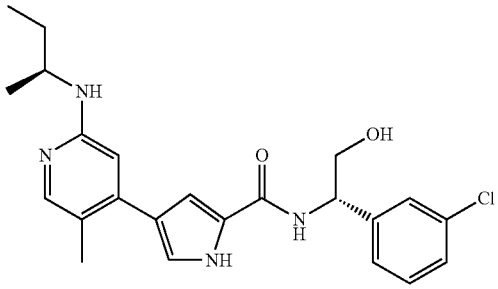
I-7
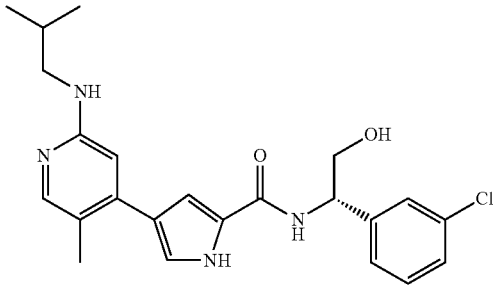
I-8
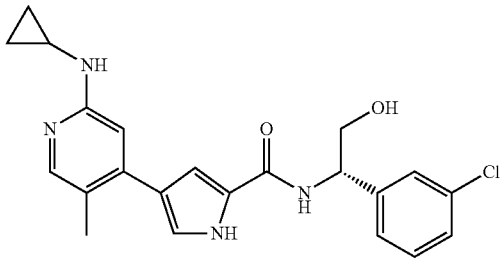
TABLE 1-continued
Examples of Compounds of Formula I:
I-9
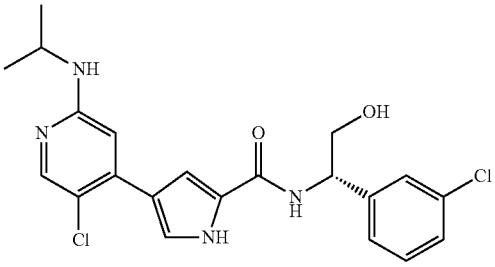
I-10
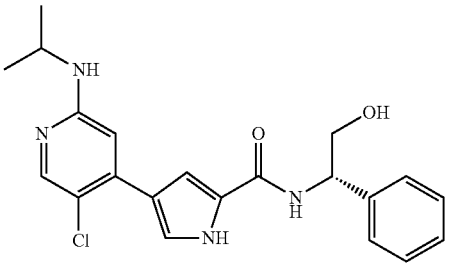
I-11
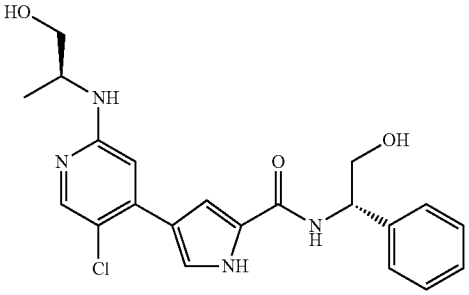
I-12
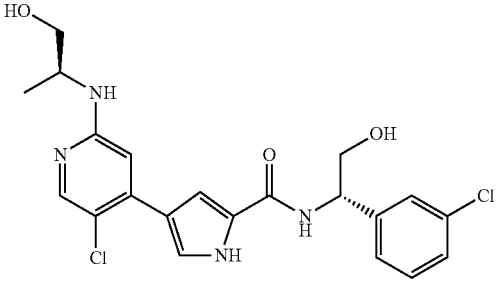
I-13
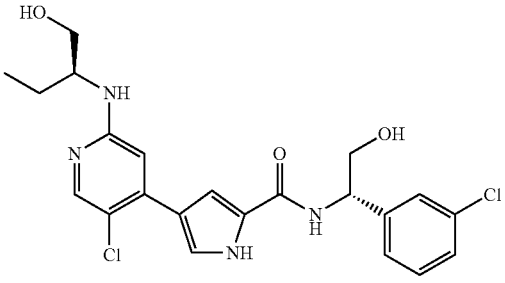

TABLE 1-continued

| Examples of Compounds of Formula I: | |
|---|---|
| 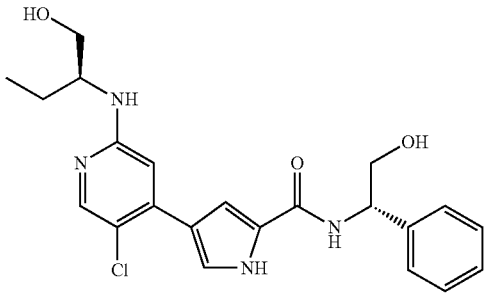 | I-14 |
| 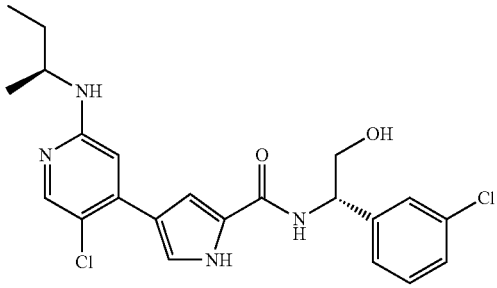 | I-15 |
| 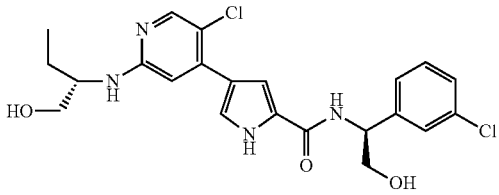 | I-16 |
| 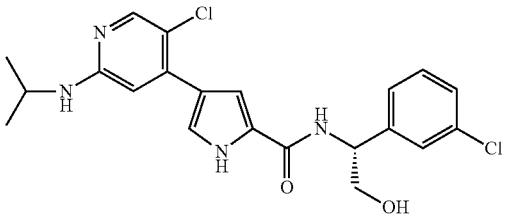 | I-17 |
| 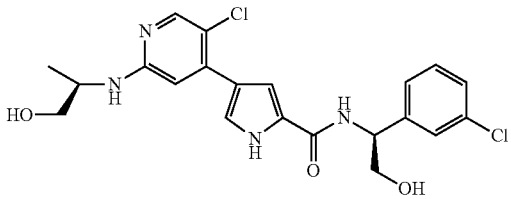 | I-18 |

4. General Methods of Providing the Present Compounds:

The compounds of this invention may be prepared or isolated in general by synthetic and/or pseudo-synthetic methods known to those skilled in the art for analogous compounds and as illustrated by the general Schemes I, II and III below and the preparative examples that follow.

Scheme I

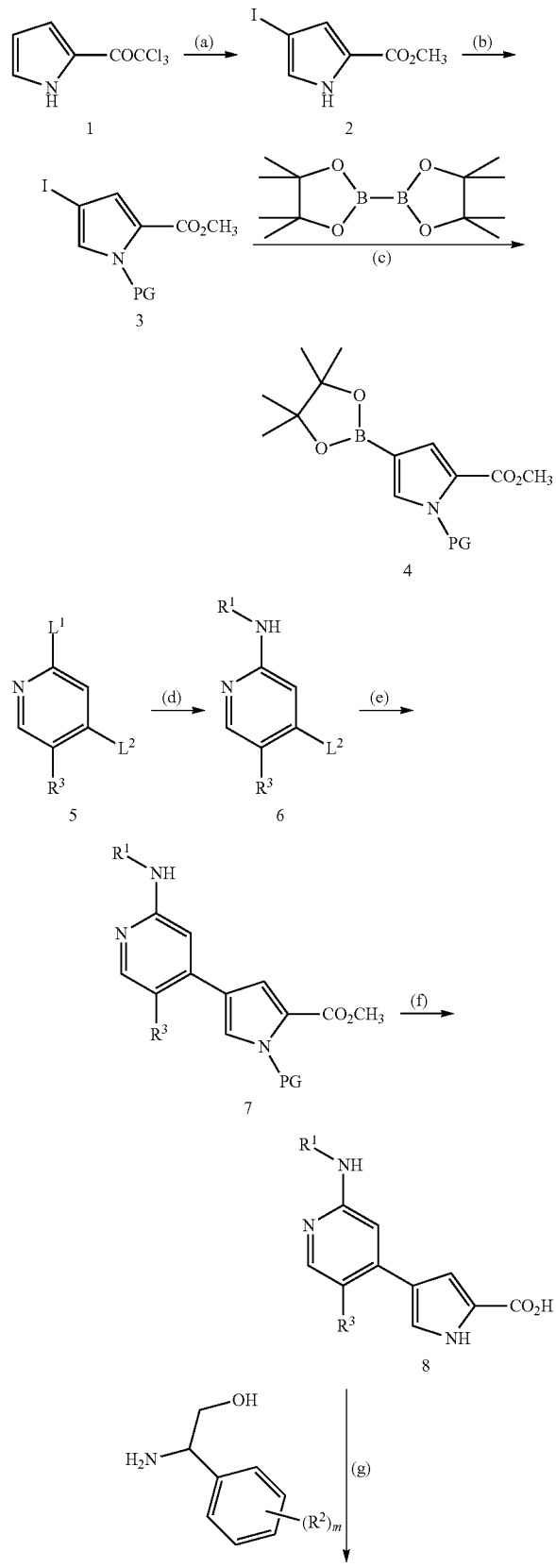

-continued

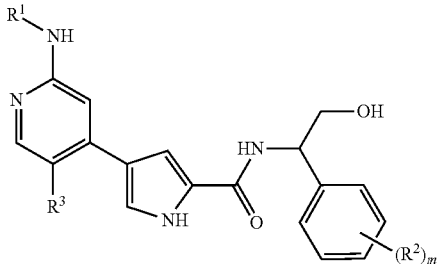

I

Reagents and conditions: (a) i ICl, $CH_2CL_2$, ii NaOMe, MeOH; (b) PG—Cl, DMAP, triethylamine; (c) Pd(dppf); (d) $R^1$—$NH_2$; (e) $Pd(PPh_3)_4$, 4; (f) deprotection/saponification; (g) coupling conditions.

General Scheme I above shows a general method for preparing the compounds of the present invention. At step (a), the pyrrole compound 1 is iodinated and esterified to form 2. At step (b), the pyrrole moiety is optionally protected at the —NH— with a suitable amino protecting group to form 3. Amino protecting groups are well known in the art and are described in detail in Protecting Groups in Organic Synthesis, Theodora W. Greene and Peter G. M. Wuts, 1991, published by John Wiley and Sons, the entirety of which is hereby incorporated by reference. The iodo moiety of compound 3 is displaced by an appropriate boronic acid or ester.As depicted above, bis(pinacolato)diborane is used to form compound 4 however other boronic esters or acids are amenable to this reaction and would be apparent to one of ordinary skill in the art.

Because the present compounds relate to a multi-substituted pyridine moiety, the order of reaction is considered and methods of activating positions on the pyridine are utilized to direct the regiochemistry. In step (d) above, the first leaving group $L^1$ may be displaced by an alcohol, amine or thiol as desired. One of ordinary skill in the art would recognize that various $L^1$ leaving groups are amenable to this reaction. Examples of such groups include, but are not limited to, halogen and activated ethers. This reaction may be followed, at step (e), by the replacement of a second leaving group $L^2$ through either a metal catalyzed coupling reaction or a nucleophilic displacement to form compound 7. One of ordinary skill in the art would recognize that various $L^2$ leaving groups are amenable to this reaction. Examples of such groups include, but are not limited to, halogen, activated ethers, boronic acid, or boronic ester.

At step (f), the protecting group on the pyrrole moiety is removed by methods suitable for removing the amino protecting group used. Depending on which amino protecting group is used, the conditions suitable for removing it may simultaneously saponify or otherwise provide the carboxylate moiety as depicted above for compound 8. If the conditions suitable for removing the amino protecting group are not suitable for providing the carboxylate compound 8, then another step may be employed. Compounds of formula I are prepared from 8 by coupling the resulting carboxylate with a desired amine as depicted at step (g). One of ordinary skill in the art would recognize that a variety of conditions are useful for said coupling reaction and can include the step of activating the carboxylate moiety of compound 8 prior to or simultaneously with treatment with the desired amine. Such conditions include, but are not limited to, those described in detail in the Examples section below.

Scheme II

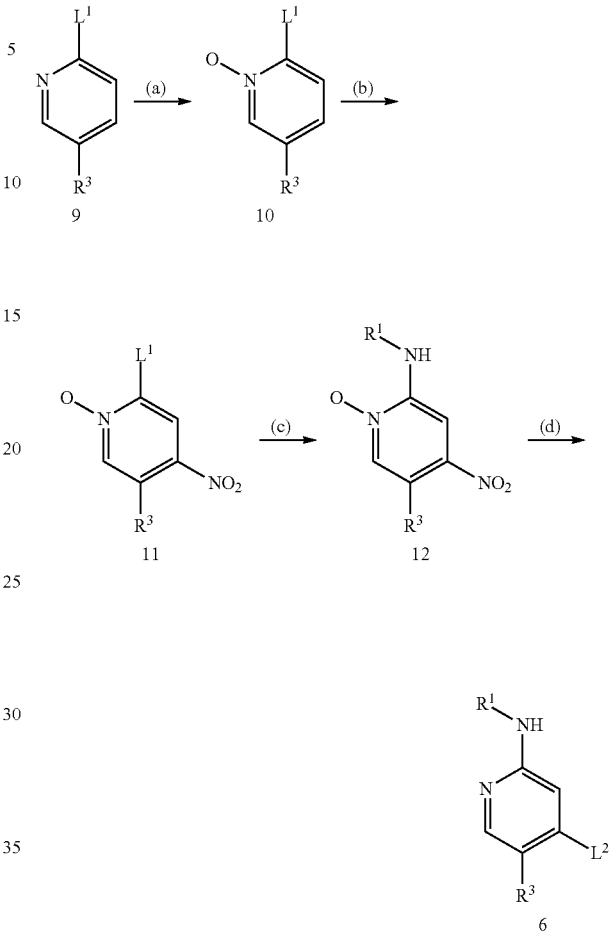

Reagents and conditions: (a) $Ac_2O/H_2O_2$; (b) $HNO_3/H_2SO_4$; (c) $R^1$—$NH_2$; (d) $L^2$.

Scheme II above depicts an alternate route to prepare intermediate compound 6 useful for preparing compounds of the present invention. At step (a), the N-oxide of compound 9 is prepared by treatment with peroxide. The N-oxide compound 10 is then treated with nitric acid to form the nitro compound 11. The $L^1$ group of 11 is displaced with the desired amine $R^1$—$NH_2$ to form 12 and then the $L^2$ group is introduced at step (d) to afford intermediate 6. Compound 6 may then be utilized to prepare compounds of the present invention according to the general Scheme I above and the Examples provided below.

Scheme III

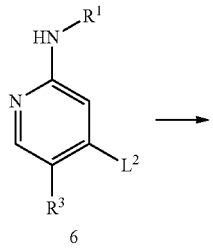

-continued

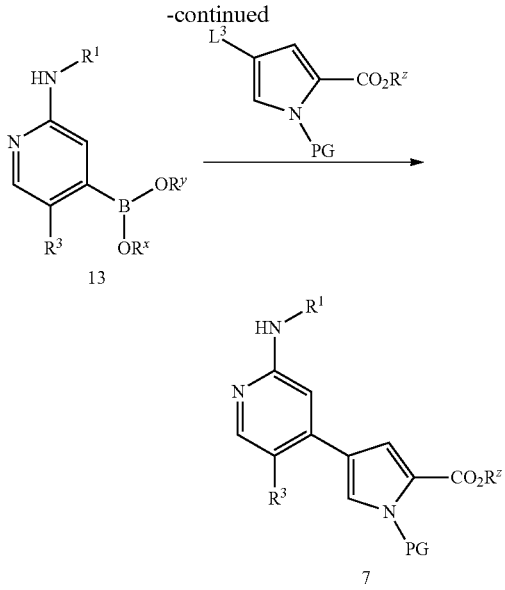

13

7

Scheme III above shows an alternate method for preparing compound 7 from 6. In this method, the $L^2$ group of the pyridinyl compound 6 is displaced by an appropriate boronic-acid or ester derivative to form 13, wherein $R^x$ and $R^y$ have the meanings as defined for compounds of formula A infra. This boronate moiety is then displaced by the $L^3$ leaving group of the pyrrole depicted above, wherein $L^3$ is a suitable leaving group, to form compound 7. Compound 7 is then used to prepare compounds of the present invention by methods set forth above in Schemes I and II, by those described in the Examples section and by methods known to one of ordinary skill in the art.

One of skill in the art would recognize that a variety of compounds of the present invention may be prepared according to the general method of Schemes I, II and III, and the synthetic Examples set forth below.

According to another embodiment, the present invention relates to a compound of formula A:

A

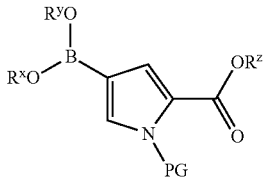

or a salt thereof, wherein:

PG is a suitable amino protecting group;

$R^z$ is a suitable carboxylate protecting group; and $R^x$ and $R^y$ are independently hydrogen or optionally substituted $C_{1-6}$ aliphatic, or:

$R^x$ and $R^y$ are taken together to form an optionally substituted 5-7 membered ring.

Suitable amino protecting groups are well known in the art and include those described in detail in Protecting Groups in Organic Synthesis, Theodora W. Greene and Peter G. M. Wuts, 1991, published by John Wiley and Sons. In certain embodiments, the PG group of A is an alkyl or aryl sulfonyl moiety. Examples of such groups include mesyl, tosyl, nosyl, brosyl, and 2,4,6-trimethylbenzenesulfonyl ("Mts"). Other such groups include Bn, PMB, Ms, Ts, $SiR_3$, MOM, BOM, Tr, Ac, $CO_2R$, $CH_2OCH_2CH_2Si(CH_3)_3$.

Suitable carboxylate protecting groups are well known in the art and are described in detail in Protecting Groups in Organic Synthesis, Theodora W. Greene and Peter G. M. Wuts, 3rd Edition, 1999, published by John Wiley and Sons. In certain embodiments, the $R^z$ group of A is an optionally substituted $C_{1-6}$ aliphatic group or an optionally substituted aryl group. Examples of suitable $R^z$ groups include methyl, ethyl, propyl, isopropyl, butyl, isobutyl, benzyl, and phenyl wherein each group is optionally substituted.

In certain embodiments, one or both of $R^x$ and $R^y$ are hydrogen.

In other embodiments, $R^x$ and $R^y$ are taken together to form an optionally substituted 5-6 membered ring. In yet other embodiments, $R^x$ and $R^y$ are taken together to form a 4,4,5,5-tetramethyldioxaborolane moiety. Other suitable boronate derivatives contemplated by the present invention include boronic acid, $B(O—C_{1-10}$ aliphatic$)_2$, and $B(O\text{-}Aryl)_2$.

According to yet another embodiment, the present invention provides a compound of formula B:

B

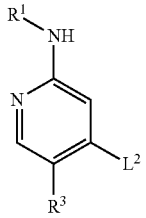

or a salt thereof, wherein:

$R^1$ is a $C_{1-6}$ aliphatic group, wherein $R^1$ is optionally substituted with up to 2 groups independently selected from —OR or —$C_{1-3}$ haloalkyl;

each R is independently hydrogen or $C_{1-4}$ aliphatic;

$R^3$ is hydrogen, $C_{1-3}$ aliphatic, fluoro, or chloro; and $L^2$ is a suitable leaving group.

In certain embodiments, the present invention provides a compound of formula B, as defined generally and in classes and subclasses described above and herein, wherein $L^2$ is not iodo when $R^3$ is chloro and $R^1$ is isopropyl.

A suitable leaving group is a chemical group that is readily displaced by a desired incoming chemical moiety. Thus, the choice of the specific suitable leaving group is predicated upon its ability to be readily displaced by the incoming chemical moiety of formula A. Suitable leaving groups are well known in the art, e.g., see, "Advanced Organic Chemistry," Jerry March, 5th Ed., pp. 351-357, John Wiley and Sons, N.Y. Such leaving groups include, but are not limited to, halogen, alkoxy, sulphonyloxy, optionally substituted alkylsulphonyl, optionally substituted alkenylsulfonyl, optionally substituted arylsulfonyl, and diazonium moieties. Examples of suitable leaving groups include chloro, iodo, bromo, fluoro, methanesulfonyl (mesyl), tosyl, triflate, nitro-phenylsulfonyl (nosyl), and bromo-phenylsulfonyl (brosyl). In certain embodiments, the $L^2$ moiety of B is iodo.

According to an alternate embodiment, the suitable leaving group may be generated in situ within the reaction medium. For example, $L^2$ in a compound of formula B may be generated in situ from a precursor of that compound of formula B wherein said precursor contains a group readily replaced by $L^2$ in situ. In a specific illustration of such a replacement, said precursor of a compound of formula B contains a group (for example, a chloro group or hydroxyl group) which is replaced in situ by $L^2$, such as an iodo group. The source of the iodo group may be, e.g., sodium iodide. Such an in situ generation of a suitable leaving group is well known in the art, e.g., see, "Advanced Organic Chemistry," Jerry March, pp. 430-431, 5th Ed., John Wiley and Sons, N.Y.

According to certain embodiments, the $R^1$ moiety of formula B, is $C_{1-4}$ aliphatic optionally substituted with —OR or —$C_{1-3}$ haloalkyl. In certain embodiments, the $R^1$ moiety of formula B is $C_{1-4}$ aliphatic optionally substituted with —OH, —$CH_2F$, —$CHF_2$, or —$CF_3$. In other embodiments, the $R^1$ moiety of formula B is $C_{1-4}$ aliphatic optionally substituted with —OH. In yet other embodiments, $R^1$ is unsubstituted.

According to another embodiment, the $R^1$ moiety of formula B is isopropyl, 2-butyl, cyclopropyl, or ethyl, wherein each moiety is optionally substituted with —OH or —$CF_3$.

In other embodiments, the $R^3$ moiety of formula B is hydrogen, methyl, or chloro.

A compound of formula B may be prepared from a compound of formula B':

B'

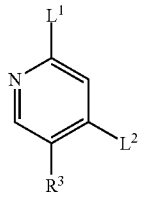

or a salt thereof, wherein:

$R^3$ is hydrogen, $C_{1-3}$ aliphatic, fluoro, or chloro; and $L^1$ and $L^2$ are each independently a suitable leaving group.

In certain embodiments, the present invention provides a compound of formula B', as defined generally and in classes and subclasses described above and herein, wherein $L^2$ is not a boronate moiety when $R^3$ is chloro and $R^1$ is fluoro.

In certain embodiments, a compound of B' is provided wherein $L^2$ is —$B(OR^x)(OR^y)$. In other embodiments, one or both of $R^x$ and $R^y$ are hydrogen. In other embodiments, $R^x$ and $R^y$ are taken together to form an optionally substituted 5-6 membered ring. In yet other embodiments, $R^x$ and $R^y$ are taken together to form a 4,4,5,5-tetramethyldioxaborolane moiety.

As described above, a suitable leaving group is a chemical group that is readily displaced by a desired incoming chemical moiety. Suitable leaving groups are well known in the art, e.g., see, "Advanced Organic Chemistry," Jerry March, 5th Ed., pp. 351-357, John Wiley and Sons, N.Y. Such leaving groups include, but are not limited to, halogen, alkoxy, sulphonyloxy, optionally substituted alkylsulphonyl, optionally substituted alkenylsulfonyl, optionally substituted arylsulfonyl, and diazonium moieties. Examples of suitable leaving groups include chloro, iodo, bromo, fluoro, methanesulfonyl (mesyl), tosyl, triflate, nitro-phenylsulfonyl (nosyl), and bromo-phenylsulfonyl (brosyl). In certain embodiments, the $L^1$ moiety of B' is halogen. In other embodiment, the $L^1$ moiety of B' is an optionally substituted alkylsulphonyl, optionally substituted alkenylsulfonyl, or optionally substituted arylsulfonyl group. In other embodiments, the $L^1$ moiety of B' is fluoro.

According to an alternate embodiment, the suitable leaving group may be generated in situ within the reaction medium. For example, $L^1$ or $L^2$ moieties in a compound of formula B' may be generated in situ from a precursor of that compound of formula B' wherein said precursor contains a group readily replaced by $L^1$ or $L^2$ in situ. Such an in situ generation of a suitable leaving group is well known in the art, e.g., see, "Advanced Organic Chemistry," Jerry March, pp. 430-431, 5th Ed., John Wiley and Sons, N.Y.

According to another embodiment, the present invention provides a method for preparing a compound of formula B:

B

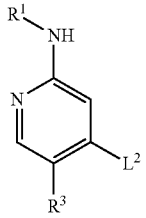

or a salt thereof, comprising the step of reacting a compound of formula B':

B'

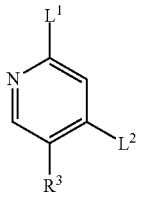

or a salt thereof, with a compound of formula $R^1$—$NH_2$ wherein said reaction is performed in a suitable medium and wherein:

$R^1$ is a $C_{1-6}$ aliphatic group, wherein $R^1$ is optionally substituted with up to 2 groups independently selected from —OR or —$C_{1-3}$ haloalkyl;

R is hydrogen or $C_{1-4}$ aliphatic;

$R^3$ is hydrogen, $C_{1-3}$ aliphatic, fluoro, or chloro; and $L^1$ and $L^2$ are each independently a suitable leaving group.

In certain embodiments, said reaction is optionally performed in the presence of a suitable base. One of ordinary skill would recognize that the displacement of a leaving group by an amino moiety is achieved either with or without the presence of a suitable base. Such suitable bases are well known in the art and include organic and inorganic bases.

A suitable medium is a solvent or a solvent mixture that, in combination with the combined compounds, may facilitate the progress of the reaction therebetween. The suitable solvent may solubilize one or more of the reaction components, or, alternatively, the suitable solvent may facilitate the agitation of a suspension of one or more of the reaction components. Examples of suitable solvents useful in the present invention are a protic solvent, a halogenated hydrocarbon, an ether, an aromatic hydrocarbon, a polar or a non-polar aprotic solvent, or any mixtures thereof. Such mixtures include, for example, mixtures of protic and non-protic solvents such as benzene/methanol/water; benzene/water; DME/water, and the like.

These and other such suitable solvents are well known in the art, e.g., see, "Advanced Organic Chemistry", Jerry March, 5th edition, John Wiley and Sons, N.Y.

According to yet another embodiment, one or more reagents may perform as the suitable solvent. For example, an organic base such as triethylamine or diisopropylethylamine, if utilized in said reaction, may serve as the solvent in addition to its role as a basifying reagent.

In certain embodiments, the present invention provides a compound of formula B' wherein $R^1$ and $R^3$ are as defined generally and in classes and subclasses described above and herein.

According to another aspect, the present invention provides a compound of formula C:

C

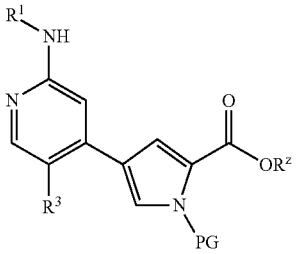

or a salt thereof, wherein:

PG is a suitable amino protecting group;

$R^z$ is a suitable carboxylate protecting group;

$R^1$ is a $C_{1-6}$ aliphatic group, wherein $R^1$ is optionally substituted with up to 2 groups independently selected from —OR or —$C_{1-3}$ haloalkyl;

each R is independently hydrogen or $C_{1-4}$ aliphatic; and $R^3$ is hydrogen, $C_{1-3}$ aliphatic, fluoro, or chloro.

As noted above, suitable amino protecting groups are well known in the art and include those described in detail in Protecting Groups in Organic Synthesis, Theodora W. Greene and Peter G. M. Wuts, 1991, published by John Wiley and Sons. In certain embodiments, the PG group of C is an alkyl or aryl sulfonyl moiety. Examples of such groups include mesyl, tosyl, nosyl, brosyl, and 2,4,6-trimethylbenzenesulfonyl ("Mts").

Suitable carboxylate protecting groups are well known in the art and are described in detail in Protecting Groups in Organic Synthesis, Theodora W. Greene and Peter G. M. Wuts, 1991, published by John Wiley and Sons. In certain embodiments, the $R^z$ group of C is an optionally substituted $C_{1-6}$ aliphatic group or an optionally substituted aryl group. Examples of suitable $R^z$ groups include methyl, ethyl, propyl, isopropyl, butyl, isobutyl, benzyl, and phenyl wherein each group is optionally substituted.

According to certain embodiments, the $R^1$ moiety of formula C, is $C_{1-4}$ aliphatic optionally substituted with —OR or —$C_{1-3}$ haloalkyl. In certain embodiments, the $R^1$ moiety of formula C is $C_{1-4}$ aliphatic optionally substituted with —OH, —$CH_2F$, —$CHF_2$, or —$CF_3$. In other embodiments, the $R^1$ moiety of formula C is $C_{1-4}$ aliphatic optionally substituted with —OH. In yet other embodiments, $R^1$ is unsubstituted.

According to another embodiment, the $R^1$ moiety of formula C is isopropyl, 2-butyl, cyclopropyl, or ethyl, wherein each moiety is optionally substituted with —OH or —$CF_3$.

In other embodiments, the $R^3$ moiety of formula C is hydrogen, methyl, or chloro.

Yet another aspect of the present invention relates to a method for preparing a compound of formula C:

C

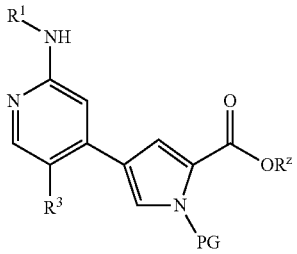

or a salt thereof, comprising the step of reacting a compound of formula A:

A

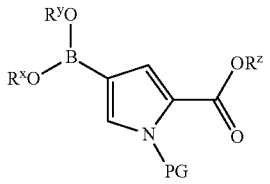

or a salt thereof, with a compound of formula B:

B

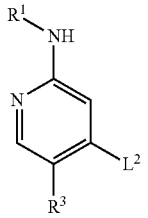

or a salt thereof, wherein said reaction is performed in a suitable medium and wherein:

PG is a suitable amino protecting group;

$L^2$ is a suitable leaving group.

$R^z$ is a suitable carboxylate protecting group;

$R^x$ and $R^y$ are independently hydrogen or optionally substituted $C_{1-6}$ aliphatic, or:

$R^x$ and $R^y$ are taken together to form an optionally substituted 5-7 membered ring;

$R^1$ is a $C_{1-6}$ aliphatic group, wherein $R^1$ is optionally substituted with up to 2 groups independently selected from —OR or —$C_{1-3}$ haloalkyl;

each R is independently hydrogen or $C_{1-4}$ aliphatic; and $R^3$ is hydrogen, $C_{1-3}$ aliphatic, fluoro, or chloro.

In certain embodiments, said reaction is performed in the presence of Ni (II), Pd (O), or Pd(II) where each catalyst may be associated with a ligand such as ferrocene or phosphine based ligands. In other embodiments, said reaction is performed in the presence of $Pd(PPh_3)_4$. A suitable medium is a solvent or a solvent mixture that, in combination with the combined compounds, may facilitate the progress of the reaction therebetween. The suitable solvent may solubilize one or more of the reaction components, or,alternatively, the suitable solvent may facilitate the agitation of a suspension of one or more of the reaction components.

Examples of suitable solvents useful in the present invention are a protic solvent, a halogenated hydrocarbon, an ether, an aromatic hydrocarbon, a polar or a non-polar aprotic solvent, or any mixtures thereof. Such mixtures include, for example, mixtures of protic and non-protic solvents such as benzene/methanol/water; benzene/water; DME/water, and the like.

These and other such suitable solvents are well known in the art, e.g., see, "Advanced Organic Chemistry", Jerry March, 5th edition, John Wiley and Sons, N.Y.

In certain embodiments, the reaction between compounds A and B to form C is performed in a mixture of DME and water.

In certain embodiments, the reaction between compounds A and B to form C is performed at a temperature ranging from about 20° C. to 150° C. In other embodiments, the reaction between compounds A and B to form C is performed with microwave irradiation at a temperature ranging from about 100° C. to 250° C.

In still other embodiments, the reaction between compounds A and B to form C is performed at a somewhat basic pH.

According to another embodiment, the present invention provides a prodrug of a compound of formula I wherein said prodrug is of formula II:

II

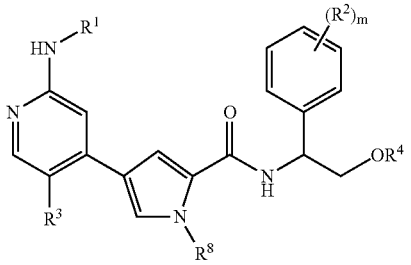

or a pharmaceutically acceptable salt thereof, wherein:

$R^1$ is a $C_{1-6}$ aliphatic group, wherein $R^1$ is optionally substituted with up to 2 groups independently selected from —OR, —$OR^4$, or —$C_{1-3}$ haloalkyl;

each R is independently hydrogen or a $C_{1-6}$ aliphatic;

each $R^2$ is independently R, fluoro, or chloro;

m is 0, 1, or 2;

$R^3$ is hydrogen, $C_{1-3}$ aliphatic, fluoro, or chloro;

each $R^4$ is independently hydrogen, —$C(R)_2O$—$R^5$, or $R^5$, provided that at least one $R^4$ or $R^8$ group is other than hydrogen;

each $R^5$ is independently —$C(O)R^6$, —$C(O)OR^6$, —C(O)-Q-$R^6$, —C(O)—$(CH_2)_n$—$C(O)OR^6$, —C(O)—$(CH_2)_n$—$C(O)N(R^7)_2$, —C(O)—$(CH_2)_n$—$CH(R^6)N(R^7)_2$, —$P(O)(OR^6)_2$;

each $R^6$ is independently hydrogen, an optionally substituted $C_{1-6}$ aliphatic group or an optionally substituted 5-8 membered saturated, partially unsaturated, or fully unsaturated ring having 0-4 heteroatoms independently selected from nitrogen, oxygen, or sulfur;

each $R^7$ is independently hydrogen, —$C(O)R^6$, —$C(O)OR^6$, —$S(O)_2R^6$, —$OR^6$, an optionally substituted $C_{1-6}$ aliphatic group or an optionally substituted 5-8 membered saturated, partially unsaturated, or fully unsaturated ring having 0-4 heteroatoms independently selected from nitrogen, oxygen, or sulfur, or:

two $R^6$ on the same nitrogen atom taken together with the nitrogen atom bound thereto form a 4-7 membered saturated, partially unsaturated, or fully unsaturated ring having 1-3 heteroatoms in addition to the nitrogen atom, independently selected from nitrogen, oxygen, or sulfur;

each n is 0-6;

Q is an optionally substituted $C_{1-10}$ alkylidene chain wherein zero to four methylene units of Q are independently replaced by —O—, —N(R)—, —S—, —S(O)—, —$S(O)_2$—, or —C(O)—; and $R^8$ is hydrogen or —$C(R)_2O$—$R^5$.

According to certain embodiments, the $R^1$ moiety of formula II is $C_{1-4}$ aliphatic optionally substituted with —OR or —$C_{1-3}$ haloalkyl. In certain embodiments, the $R^1$ moiety of formula II is $C_{1-4}$ aliphatic optionally substituted with —OH, —$CH_2F$, —$CHF_2$, or —$CF_3$. In other embodiments, the $R^1$ moiety of formula II is $C_{1-4}$ aliphatic optionally substituted with —OH. In yet other embodiments, $R^1$ is unsubstituted.

According to another embodiment, the $R^1$ moiety of formula II is isopropyl, 2-butyl, cyclopropyl, or ethyl, wherein each moiety is optionally substituted with —OH, —$CHF_2$, —$CH_2F$, or —$CF_3$. According to yet another embodiment, the $R^1$ moiety of formula II is isopropyl, 2-butyl, cyclopropyl, or ethyl, wherein each moiety is optionally substituted with —OH or —$CF_3$.

Another aspect of the present invention relates to a compound of formula II wherein each $R^2$ is independently hydrogen, $C_{1-3}$ aliphatic, or chloro. According to yet another aspect, the present invention relates to a compound of formula II wherein $R^2$ is chloro and m is 1.

In other embodiments, the $R^3$ moiety of formula II is hydrogen, methyl, or chloro.

In certain embodiments, $R^4$ is C(O)-Q-$R^6$. Still other embodiments related to a compound of formula II wherein $R^4$ is C(O)-Q-$R^6$ and Q is an optionally substituted $C_{1-8}$ alkylidene chain wherein zero to four methylene units of Q are independently replaced by —O—, —N(R)—, —S—, —S(O)—, —$S(O)_2$—, or —C(O)— and $R^6$ is as defined in general and in classes and subclasses described above and herein. According to another embodiment, Q is an optionally substituted $C_{1-8}$ alkylidene chain wherein two to four methylene units of Q are independently replaced by —O—. Such Q groups include —$CH_2OCH_2CH_2O$—, —$CH_2OCH_2CH_2OCH_2CH_2O$—, and the like.

Yet another aspect of the present invention provides a compound of formula II wherein $R^4$ is C(O)—$(CH_2)_n$—$CH(R^6)N(R^7)_2$. In certain embodiments, n is 0-2. In other embodiments, $R^6$ is an optionally substituted $C_{1-6}$ aliphatic group. Examples of such $R^6$ groups include methyl, benzyl, ethyl, isopropyl, t-butyl, and the like. The $R^7$ groups of the C(O)—$(CH_2)_n$—$CH(R^6)N(R^7)_2$ of formula II include hydrogen and an optionally substituted $C_{1-6}$ aliphatic group. Examples of such groups include methyl, benzyl, ethyl, isopropyl, t-butyl, and the like.

According to one aspect, the present invention provides a compound of formula II wherein $R^8$ is hydrogen.

According to one embodiment, $R^4$ is an L-valine ester.

In certain embodiments of the present invention, the $R^4$ group of formula II is —$P(O)(OR^6)_2$. In other embodiments, each $R^6$ is independently hydrogen or an optionally substituted $C_{1-6}$ aliphatic group. Examples of such $R^6$ groups include methyl, benzyl, ethyl, isopropyl, t-butyl, and the like. In still other embodiments, the $R^4$ group of formula II is —$P(O)(OH)_2$.

In certain embodiments, a compound of formula II provides improvement with regard to one or more physical or physiological characteristics. In other embodiments, a compound of formula II imparts improvement with regard to one or more physical and physiological characteristics.

Representative compounds of formula II are set forth in Table 2 below.

TABLE 2

II-1

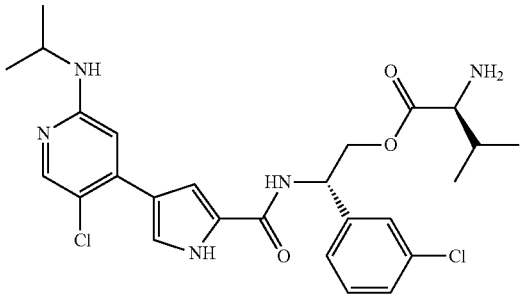

II-2

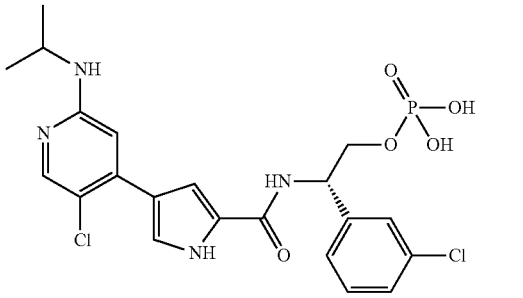

II-3

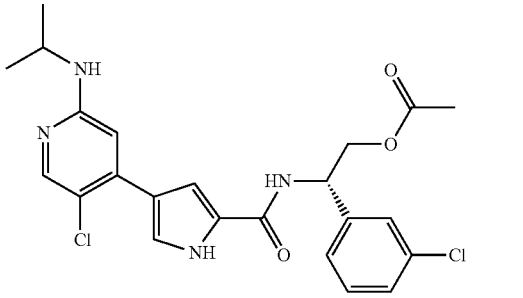

II-4

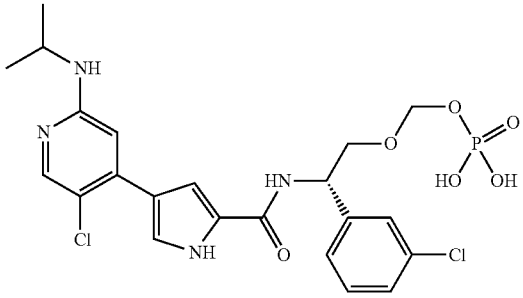

II-5

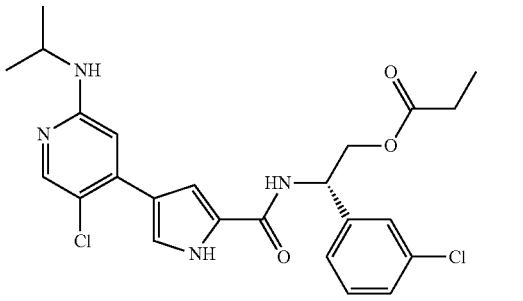

TABLE 2-continued

II-6

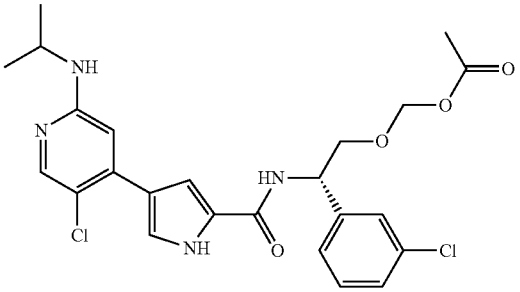

II-7

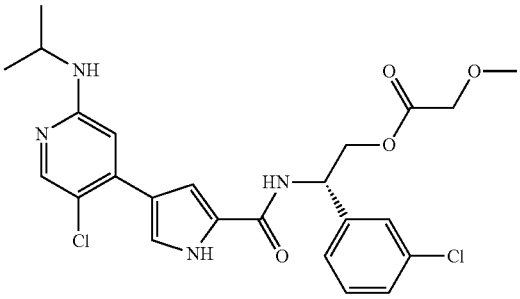

II-8

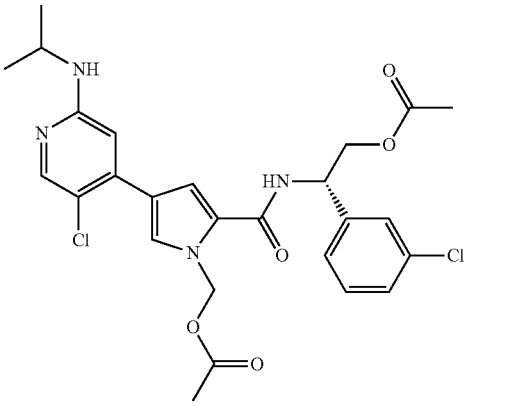

Methods of preparing such prodrugs include those set forth in detail in the Examples section infra and methods known to one or ordinary skill in the art.

5. Uses, Formulation and Administration

Pharmaceutically Acceptable Compositions

As discussed above, the present invention provides compounds that are inhibitors of protein kinases, and thus thepresent compounds are useful for the treatment of diseases, disorders, and conditions including, but not limited to cancer, autoimmune disorders, neurodegenerative and neurological disorders, schizophrenia, bone-related disorders, liver disease, and cardiac disorders. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of ERK2 protein kinase.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of cancer, an autoimmune disorder, a neurodegenerative or neurological disorder, liver disease, or a cardiac disorder is provided comprising administering an effective amount of a compound of the present invention, or a pharmaceutically acceptable composition comprising a compound of the present invention to a subject in need thereof. In certain embodiments of the present invention an "effective amount" of the compound or pharmaceutically acceptable composition is that amount effective for treatingor lessening the severity of a disease, condition, or disorder selected from cancer, an autoimmune disorder, a neurodegenerative or neurological disorder, schizophrenia, a bone-related disorder, liver disease, or a cardiac disorder. The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. Thesolid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of ERK protein kinases. In one embodiment, the compounds and compositions of the invention are inhibitors of one or both of ERK1 and ERK2 protein kinases and thus, without wishing to be bound by any particular theory, the compounds and compositions are particularly useful for treating or lessening the severity of a disease, condition, or disorder where activation of one or both of ERK1 and ERK2 protein kinases is implicated in the disease, condition, or disorder. When activation of ERK1 and/or ERK2 protein kinases is implicated in a particular disease, condition, or disorder, the disease, condition, or disorder may also be referred to as "ERK1- or ERK2-mediated disease", condition, or disease symptom. Accordingly, in another aspect, the present invention provides a method for treating or lessening the severity of a disease, condition, or disorder where activation of one or both of ERK1 and ERK2 protein kinases is implicated in said disease, condition, or disorder.

The activity of a compound utilized in this invention as an inhibitor of ERK1 and/or ERK2 protein kinases may be assayed in vitro, in vivo or in a cell line. In vitro assays include assays that determine inhibition of either the phosphorylation activity or ATPase activity of activated ERK1 or ERK2 protein kinases. Alternate in vitro assays quantitate the ability of the inhibitor to bind to ERK1 or ERK2 protein kinases. Inhibitor binding may be measured by radiolabelling the inhibitor prior to binding, isolating the inhibitor/ERK1 or inhibitor/ERK2 complex and determining the amount of radiolabel bound. Alternatively, inhibitor binding may be determined by running a competition experiment where new inhibitors are incubated with ERK1 or ERK2 protein kinases bound to known radioligands.

The term "measurably inhibit", as used herein means a measurable change in ERK1 or ERK2 protein kinase activity between a sample comprising said composition and a ERK1 or ERK2 protein kinase and an equivalent sample comprising ERK1 or ERK2 protein kinase in the absence of said composition. Such measurements of protein kinase activity are known to one of ordinary skill in the art and include those methods set forth herein below.

According to another embodiment, the invention relates to a method of inhibiting ERK1 or ERK2 protein kinase activity in a patient comprising the step of administering to said patient a compound of the present invention, or a composition comprising said compound.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein said method comprises administering to a patient in need thereof a composition according to the present invention.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another embodiment relates to a method of treating melanoma, breast cancer, colon cancer, or pancreatic cancer in a patient in need thereof.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable compositioncomprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting ERK1 or ERK2 protein kinase activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ERK1 or ERK2 protein kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

As used herein, the term "$R_t$" refers to the HPLC retention time, in minutes, associated with the compound. Unless otherwise indicated, the HPLC method utilized to obtain the reported retention time is as follows:

Column: Agilent/ZORBAX SB—C18/5 μm/3.0×150 mm/PN 883975-302/SN USBM001410

Gradient: 10-90% MeCN over 8 minutes

Flow: 1.0 mL/minute

Detection: 214 nm and 254 nm

Unless otherwise indicated, each $^1$H NMR was obtained at 500 MHz in $CDCl_3$ and compound numbers correspond to those compound numbers recited in Table 1.

Example 1

Compound I-9 was prepared as follows:

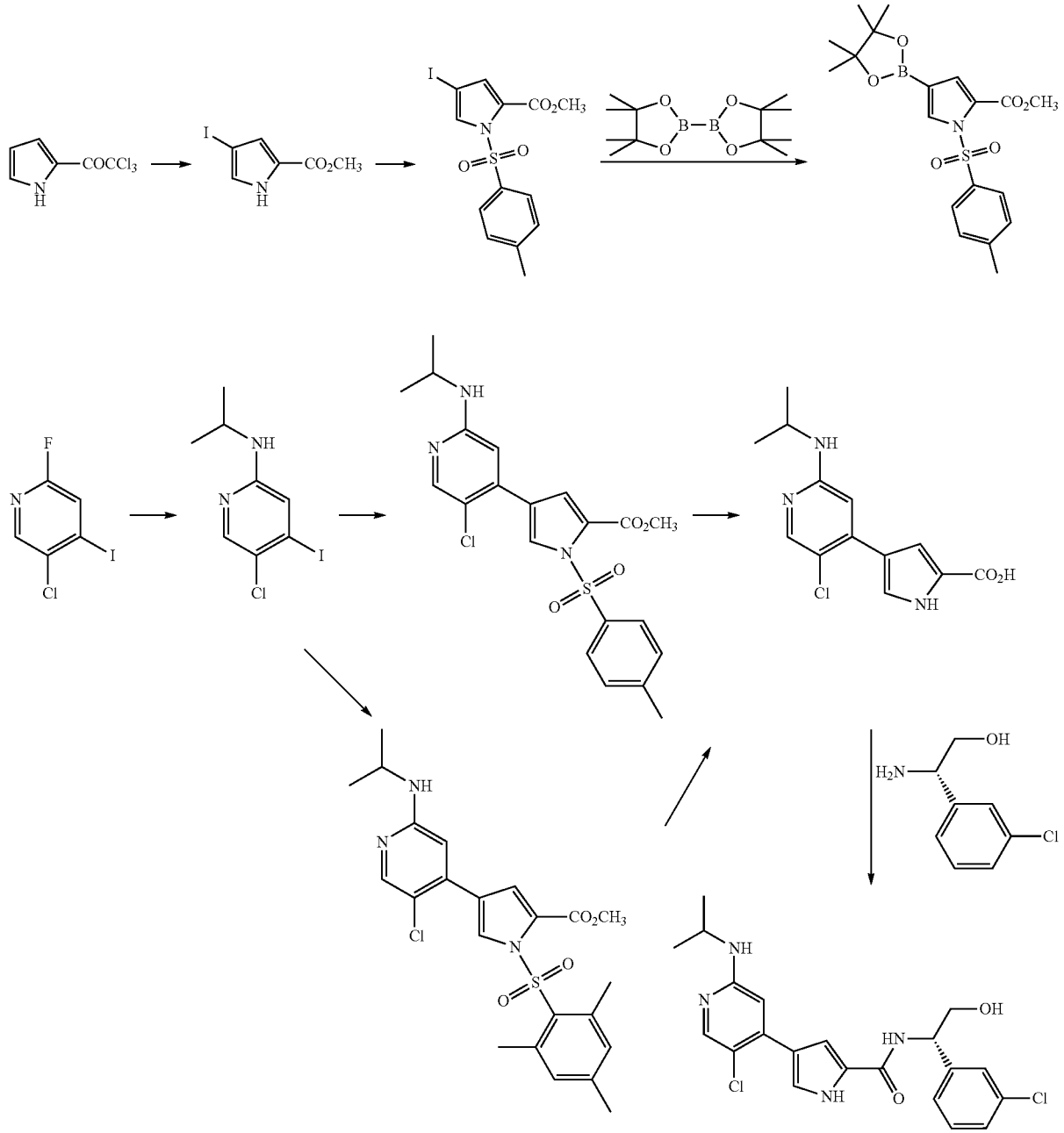

I-9

2,2,2-Trichloro-1-(4-iodo-1H-pyrrol-2-yl)ethanone: To a stirred solution of 50 g (235 mmol, 1.0 equiv.) of 2,2,2-trichloro-1-(1H-pyrrol-2-yl)-ethanone in dry dichloromethane (400 mL) under nitrogen, a solution of iodine monochloride (39 g, 240 mmol, 1.02 equivalents) in of dichloromethane (200 mL) was added dropwise. The resulting mixture was stirred at room temperature for 2 hours. The solution was washed with 10% potassium carbonate, water, 1.0 M sodium thio sulfate, saturated sodium chloride, dried over sodium sulfate, filtered, and concentrated under reduced pressure. The solid was recrystallized from hexanes/methyl acetate to afford the title compound (68.5 g, 86%) as a colorless solid (86%). MS FIA: 335.8, 337.8 ES-.

4-Iodo-1H-pyrrole-2-carboxylic acid methyl ester: To a stirred solution of 2,2,2-trichloro-1-(4-iodo-1H-pyrrol-2-yl) ethanone (68 g, 201 mmol, 1.0 equivalent) in dry methanol (400 mL) under nitrogen, was added a solution of sodium methoxide in methanol (4.37 M, 54 mL, 235 mmol, 1.2 equivalents) over 10 minutes. The resulting mixture was stirred at room temperature for 1 hour. The volatiles were removed under reduced pressure and the crude was then partitioned between water and tert-butylmethyl ether. The organic phase was separated, washed two times with water, saturated sodium chloride, dried over sodium sulfate, filtered and concentrated under vacuum to afford the title compound (48 g, 96%) as a colorless solid, that was used directly without further purification.

4-Iodo-1-(toluene-4-sulfonyl)-1H-pyrrole-2-carboxylic acid methyl ester: 4-Iodo-1H-pyrrole-2-carboxylic acid methyl ester (24.6 g, 98 mmol, 1.0 equivalent) was dissolved in dichloromethane (150 mL) and triethylamine (30 mL, 215.6 mmol, 2.2 equivalents). 4-(Dimethylamino)pyridine (1.2 g, 9.8 mmol, 0.1 equivalent) and p-toluenesulfonylchloride (20.6 g, 107.8 mmol, 1.1 equivalents) were added and the reaction mixture was stirred for 16 hours at room temperature. The reaction was quenched with 1 M HCl and the organic layer was washed with aqueous sodium bicarbonate and brine. After drying over magnesium sulfate, the solvent was removed under reduced pressure and the residue was crystallized from tert-butylmethyl ether, yielding the title compound as a pale yellow solid (30 g, 75%). $R_t$(min) 8.259 minutes.

4-(4,4,5,5-Tetramethyl-[1,3,2]dioxaborolan-2-yl)-1-(toluene-4-sulfonyl)-1H-pyrrole-2-carboxylic acid methyl ester: To a degassed solution of 4-iodo-1-(toluene-4-sulfonyl)-1H-pyrrole-2-carboxylic acid methyl ester (20 g, 49.4 mmol, 1.0 equivalent) and bis(pinacolato)diborane (15 g, 65 mmol, 1.3 equivalents) in DMF (200 mL) under nitrogen, was added dichloro[1,1'-bis(diphenylphosphino)ferrocene] palladium (II) dichloromethane adduct (3.6 g, 4.9 mmol, 0.1 equivalent). The reaction mixture was then stirred at 80° C. for 18 hours. After removing the DMF under reduced pressure, the resulting thick oil residue was suspended in diethyl ether (500 mL) and a solid precipitated immediately. This solid was removed by filtration and the filtrate was washed with 1M HCl, water, brine and dried over $MgSO_4$. Concentration afforded the title compound as a white solid and used without further purification (10 g, 50%). LC/MS: $R_t$(min) 4.6; 406.4 ES+. MS FIA: 406.2 ES+. $^1$HNMR δ 1.2 (s, 12H), 2.35 (s, 3H), 3.8 (s, 3H), 7.2 (m, 3H), 7.8 (d, 2H), 8.0 (s, 1H).

N,N'-2-(5-Chloro-4-iodo-pyridyl)-isopropylamine:

Method A. (Microwave)

In a 10 mL microwave tube, 5-chloro-2-fluoro-4-iodopyridine (1.0 g, 3.9 mmol, 1.0 equivalent) was dissolved in DMSO (4.0 mL) and then ispropylamine (0.99 mL, 11.7 mmol, 3.0 equivalents) was added. The tube was sealed and placed under microwave irradiation for 600 sec at 150° C.

This reaction was repeated six times. The reaction mixtures were combined, then diluted in ethyl acetate and washed with water. After drying over sodium sulfate, the solvent was evaporated to afford the title compound as a thick brown oil (5.6 g, 80%) which was used directly without further purification. $R_t$(min) 4.614; MS FIA: 296.9 ES+. $^1$HNMRssssssss δ 1.25 (d, 6H), 3.65 (m, 1H), 7.15 (s, 1H), 7.75 (s, 1H).

Method B: (Thermal)

5-Chloro-2-fluoro-4-iodopyridine (400 mg, 1.55 mmol, 1.0 equivalent) was dissolved in ethanol (5.0 mL) and then isopropylamine (0.66 mL, 7.8 mmol, 5.0 equivalents) was added. The resulting solution was stirred at 80° C. for 48 hours. The reaction mixture was then diluted in ethyl acetate and washed with water. After drying over sodium sulfate, the solvent was evaporated and a thick brown oil was obtained, which was then purified by flash chromatography on silica gel eluting with mixtures of hexanes/ethyl acetate (from 99:1 to 80:20) to afford the title compound as a pale yellow solid (96 mg, 21%).

4-(5-Chloro-2-isopropylaminopyridin-4-yl)-1-(toluene-4-sulfonyl)-1H-pyrrole-2-carboxylic acid methyl ester: To a solution of N,N'-2-(5-chloro-4-iodo-pyridyl)-isopropylamine (0.53 g, 1.8 mmol, 1.0 equivalent) and 4-(4,4,5,5-tetramethyl-[1,3,2]dioxaborolan-2-yl)-1-(toluene-4-sulfonyl)-1H-pyrrole-2-carboxylic acid methyl ester (0.78 g, 1.8 mmol, 1.0 equivalent) in DME (4.0 mL) was added a solution of aqueous 2 M sodium carbonate (1.0 mL) followed by $Pd(PPh_3)_4$ (0.21 mg, 0.18 mmol, 0.1 equivalent). The microwave tube was sealed and the reaction mixture was irradiated by microwave for 1800 sec. at 170° C. The crude of six reactions were combined and diluted in ethyl acetate and washed with water. After drying the organic layer with sodium sulfate, the solvent was removed and the resulting thick oil was adsorbed on silica gel. The crude was then purified by flash chromatography on silica, eluting with hexanes/ethyl acetate mixtures (from 99:1 to 70:30) to afford the title compound as a yellow solid (3.1 g, 61% over two steps). $R_t$(min) 6.556. MS FIA: 448.1 ES+. $^1$HNMR δ 1.45 (d, 6H), 2.5 (s, 3H), 3.81 (s, 3H), 6.8 (s, 1H), 7.35 (s, 1H), 7.4 (d, 2H), 8.0 (m, 3H), 8.3 (s, 1H).

4-(5-Chloro-2-isopropylaminopyridin-4-yl)-1-(2,4,6-trimethylbenzenesulfonyl)-1H-pyrrole-2-carboxylic acid methyl ester: To a solution of N,N'-2-(5-chloro-4-iodopyridyl)-isopropylamine (96 mg, 0.32 mmol, 1.0 equivalent) and 4-(4,4,5,5-tetramethyl[1,3,2]dioxaborolan-2-yl)-1-(2,4,6-trimethylbenzenesulfonyl)-1H-pyrrole-2-carboxylic acid methyl ester (152 mg, 0.35 mmol, 1.1 equivalents) in DME (2 mL), was added a solution of aqueous 2 M sodium carbonate (0.2 mL) followed by $Pd(PPh_3)_4$ (37 mg, 0.032 mmol, 0.1 equivalent). The reaction mixture was stirred at 80° C. for 16 hours. The crude was diluted in ethyl acetate and washed with water. After drying the organic layer with sodium sulfate, the solvent was removed and the resulting thick oil was adsorbed on silica gel. The crude was then purified by flash chromatography on silica, eluting with hexanes/ethyl acetate mixtures (from 99:1 to 80:20) to afford the title compound as a yellow solid (65 mg, 43%). $R_t$(min) 7.290. MS FIA:476.1 ES+.

4-(5-Chloro-2-isopropylaminopyridin-4-yl)-1H-pyrrole-2-carboxylic acid:

Method A. (Microwave)

A solution of 4-(5-chloro-2-isopropylaminopyridin-4-yl)-1-(toluene-4-sulfonyl)-1H-pyrrole-2-carboxylic acid methyl ester (3.1 g, 6.9 mmol, 1.0 equivalent) in THF (2.0 mL) was added to a solution of lithium hydroxide monohydrated (710 mg, 17.3 mmol, 2.5 equivalents) in water (3.0 mL). The microwave tube was sealed and the reaction mixture was irradiated by microwave for 1200 sec. at 150° C. The crude solution was acidified with aqueous 6N HCl. The solvent was evaporated off to afford the title compound which was used directly without further purification. $R_t$(min): 3.574. FIA MS: 279.9 ES+; 278.2 ES−.

Method B: (Thermal)

A solution of 4-(5-chloro-2-isopropylaminopyridin-4-yl)-1-(2,4,6-trimethylbenzenesulfonyl)-1H-pyrrole-2-carboxylic acid methyl ester (0.69 g, 1.4 mmol, 1.0 equivalent) in THF (3.0 mL) was added to a solution of lithium hydroxide monohydrated (1.19 g, 29 mmol, 20.0 equivalents) in water (3.0 mL). The mixture was then refluxed for 8 hours. The crude solution was acidified with aqueous 6N HCl until cloudy, the organic solvent was partially removed and the product precipitated. The title compound was isolated by filtration and washed with water and diethyl ether, yielding a white solid (0.38 g, 96%).

4-(5-Chloro-2-isopropylaminopyridin-4-yl)-1H-pyrrole-2-carboxylic acid [1-(3-chlorophenyl)-2-hydroxyethyl] amide: To a suspension of 4-(5-chloro-2-isopropylaminopyridin-4-yl)-1H-pyrrole-2-carboxylic acid (1.93 g, 6.9 mmol, 1.0 equivalent) in DMF (5.0 mL) was added EDCI (1.45 g, 7.6 mmol, 1.1 equivalents), HOBt (0.94 g, 6.9 mmol, 1.0 equivalent) and (S)-3-chlorophenylglycynol (1.58 g, 7.6 mmol, 1.1 equivalents). Diisopropylethylamine (2.7 mL) was then added and the resulting mixture was stirred a room temperature overnight. The mixture was then poured into water and extracted with ethyl acetate. After drying over sodium sulfate, the solvent was removed and the crude was adsorbed on silica gel. Purification was effected by flash chromatography on silica, eluting with mixtures of hexanes/acetone (from 80:20 to 60:40) to afford the title compound as white solid (1.9 g, 64%). $R_t$(min) 4.981 s. FIA MS: 433.1 ES+; 431.2 ES−. $^1$HNMR ($CD_3OD$) δ 1.31 (d, 6H), 3.85 (m, 3H), 5.15 (t, 1H), 7.01 (s, 1H), 7.25 (m, 3H), 7.4 (s, 1H), 7.45 (s, 1H), 7.7 (s, 1H), 7.95 (s, 1H).

Example 2

Compound I-9 was also prepared according to following alternate method:

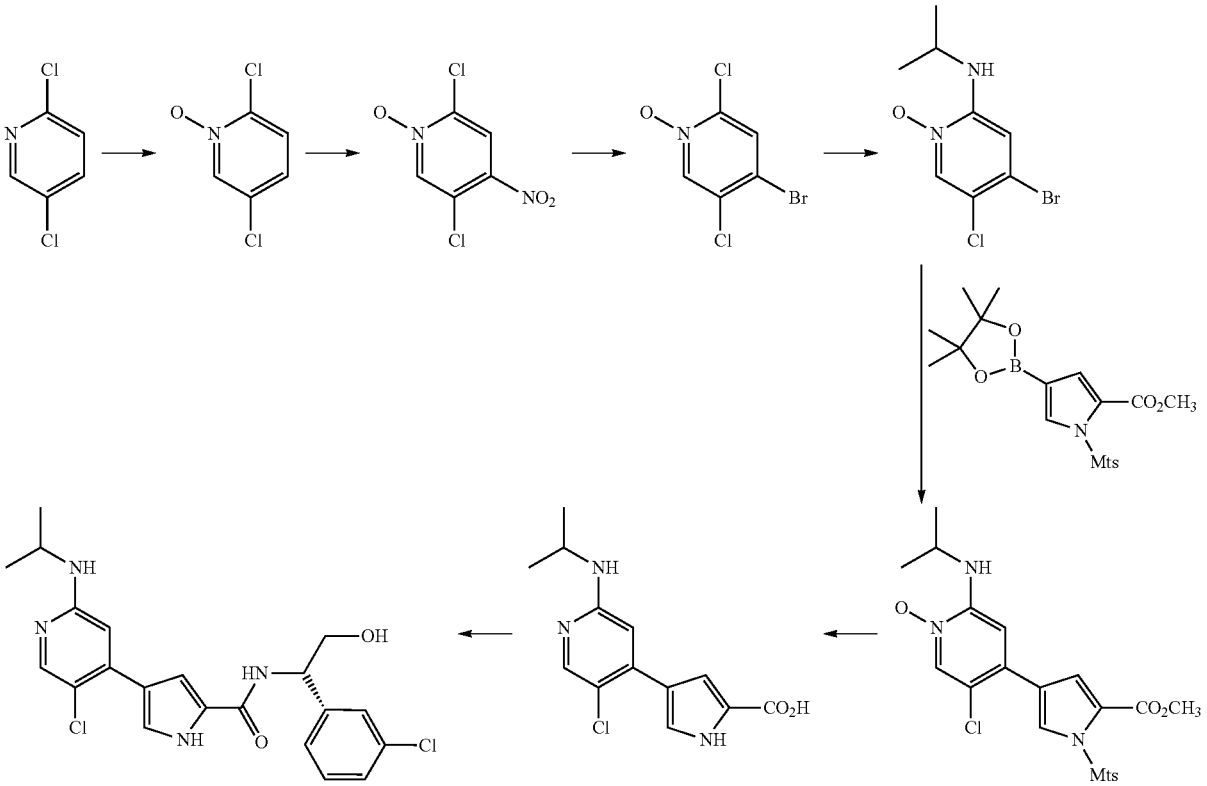

2,5-Dichloro-4-nitropyridine N-oxide: To a suspension of 2-chloro-5-chloropyridine (10 g, 0.067 mol) in acetic anhydride (25 mL) was added hydrogen peroxide 30% (25 mL) in small portions. This mixture was stirred at room temperature for 24 hours and then heated at 60° C. for 30 hours. After removing the excess of acetic acid under reduced pressure, the residue was added in small portions to concentrated sulfuric acid (15 mL). The resulting solution was added to a mixture of concentrated sulfuric acid (15 mL) and fuming nitric acid (25 mL) and then heated at 100° C. for 90 minutes. The reaction mixture was poured on ice, neutralized with solid ammonium carbonate and finally with aqueous ammonia until a basic pH was obtained and A precipitate formed. The precipitate was collected by filtration to afford the title compound as a pale yellow solid (3.1 g), $R_t$(min) 3.75. MS FIA shows no peak. $^1$HNMR (DMSO-$d_6$) δ 8.78 (s, 1H), 9.15 (s, 1H).

4-Bromo-2-chloro-5-N-isopropylpyridin-2-amine N-oxide: To 2,5-dichloro-4-nitropyridine N-oxide (400 mg, 1.9 mmol) was added acetyl bromide (2 mL) very slowly. The reaction mixture was then heated at 80° C. for 10 minutes. The solvent was removed under a stream of nitrogen and the crude product was dried under high vacuum. The crude material (165 mg, 0.62 mmol) was dissolved in ethanol (2 mL), iso-propylamine (0.53 mL) added and the resulting mixture was heated at 80° C. for 2 hours. The crude solution was then purified by reversed phase HPLC (acetonitrile/water/TFA 1%) to afford the title compound as a pale yellow solid (60 mg, 36.6%). $R_t$(min) 5.275. MS FIA264.8, 266.9 ES+.

4-(5-chloro-2-isopropylaminopyridin-4-yl)-1H-pyrrole-2-carboxylic acid [1-(3-chlorophenyl)-2-hydroxyethyl] amide (1-9): 4-Bromo-2-chloro-5-N-isopropylpyridin-2-amine N-oxide (25 mg, 0.094 mmol, 1.0 equivalent) and 4-(4,4,5,5-tetramethyl-[1,3,2]dioxaborolan-2-yl)-1-(2,4,6-trimethylbenzensulfonyl)-1H-pyrrole-2-carboxylic acid methyl ester (39 mg, 0.094 mmol, 1.0 equivalent) were dissolved in benzene (5 mL) then aqueous 2M $Na_2CO_3$ (1 mL) and $Pd(PPh_3)_4$ (115.6 mg, 0.1 mmol, 0.2 equivalent) were added and the resulting suspension was heated at reflux at 80° C. for 16 hours. The reaction mixture was diluted in ethyl acetate, washed with water and dried over anhydrous sodium sulfate to afford 4-(5-chloro-2-isopropylamino-pyridin-4-yl)-1-(2,4,6-trimethyl-benzenesulfonyl)-1H-pyrrole-2-carboxylic acid methyl ester N-oxide ($R_t$(min) 6.859. MS FIA: 492.0 ES+) which was then treated with a 2 M solution of $PCl_3$ in dichloromethane (1 mL) at room temperature. After 10 minutes, the solvent was removed under a stream of nitrogen and the crude oil was dissolved in methanol (1 mL) and aqueous 1 M NaOH (1 mL). The resulting mixture was heated at reflux for 16 hours then the crude solution was acidified using aqueous 1 M HCl and the solvent was removed. The resulting 4-(5-chloro-2-isopropylamino-pyridin-4-yl)-1H-pyrrole-2-carboxylic acid ($R_t$(min) 3.527. MS FIA: 279.4 ES+; 278.2 Es−) was suspended in DMF (3 mL) together with EDCI (36 mg, 0.19 mmol, 2 equivalents), HOBt (26 mg, 0.19 mmol, 2 equivalents), (S)-3-chlorophenylglycinol HCl salt (59 mg, 0.28 mmol, 3 equivalents) and DIEA (0.12 mL, 0.75 mmol, 8 equivalents). The resulting mixture was stirred at room temperature for 16 hours. The reaction mixture was diluted in ethyl acetate, washed with water and dried over sodium sulfate. After removing the solvent under reduced pressure, the crude product was purified by reversed phase HPLC (acetonitrile/water/TFA 1%) to afford the title compound as a white solid (4.8 mg, 8.1%).

Example 3

Compound 1-3 was prepared as follows:

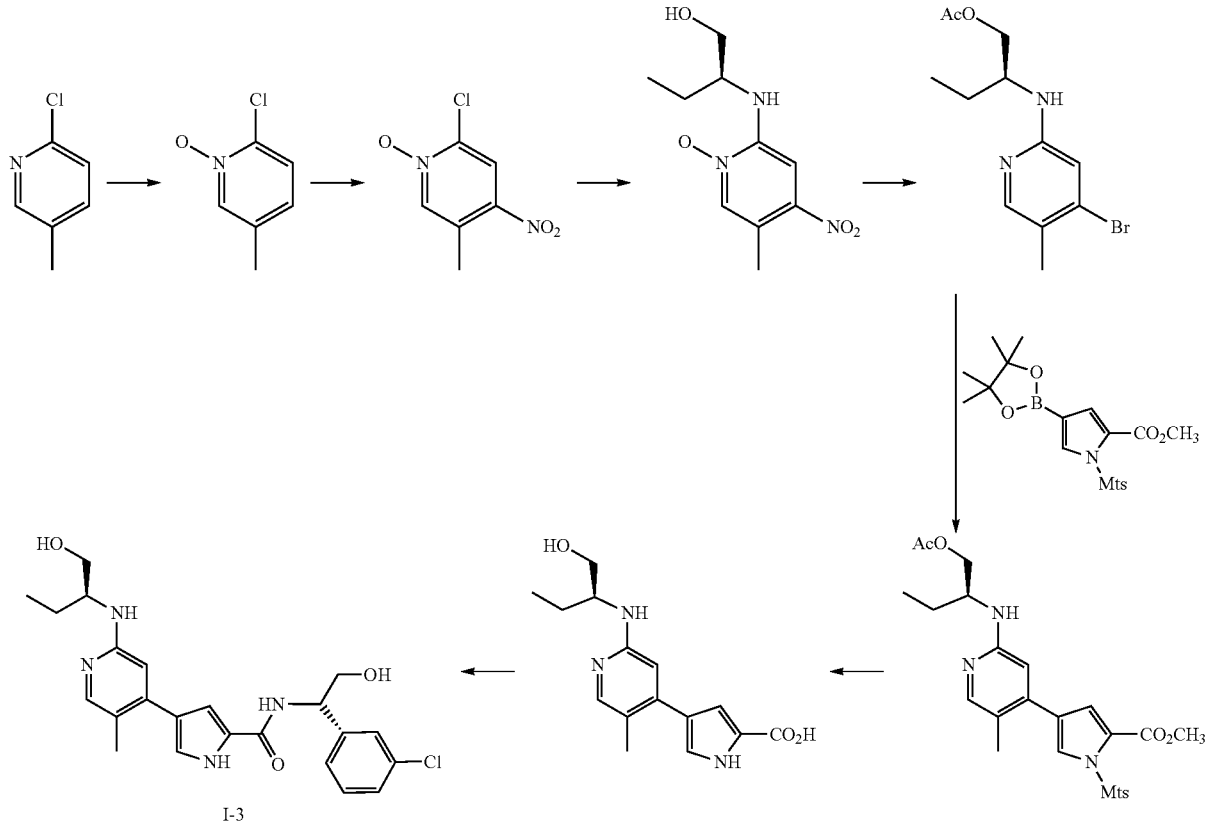

2-Chloro-5-methyl-4-nitropyridine N-oxide: The title compound was prepared in a manner substantially similar to that described by Z. Talik, A. Puszko, Roczniki Chemii Ann. Soc. Chim. Polonorum 1976, 50, 2209, as follows. To a suspension of 2-chloro-5-methylpyridine (10 g, 0.078 mol) in acetic anhydride (25 mL) was added hydrogen peroxide 30% (25 mL) in small portions. This mixture was stirred at room temperature for 24 hours and then heated at 60° C. for 30 hours. After removing the excess acetic acid under reduced pressure, the residue was added in small portions to concentrated sulfuric acid (15 mL). The resulting solution was added to a mixture of concentrated sulfuric acid (15 mL) and fuming nitric acid (25 mL) and then heated at 100° C. for 90 minutes. The reaction mixture was poured onto ice, neutralized with solid ammonium carbonate and finally with aqueos ammonia until a basic pH was obtained and a precipitate formed. This precipitate was collected by filtration to afford the title compound as a pale yellow solid (9.4 g, 0.050 mol, $R_t$(min) 3.272, FIA ES+ 188.9, ES− 188.0).

2-((S)-1-Hydroxymethylpropylamino)-5-methyl-4-nitropyridine N-oxide: 2-Chloro-5-methyl-4-nitropyridine N-oxide (200 mg, 1.06 mmol, 1.0 equivalent) was dissolved in ethanol (1.5 mL). (S)-2-Aminobutanol (284 mg, 3.2 mmol, 3.0 equivalent) was then added and the resulting mixture was refluxed for 16 hours. The crude solution was then purified by reversed phase HPLC (acetonitrile/water/TFA) to afford the title compound as a brown solid (146 mg, 0.61 mmol, $R_t$(min) 3.787; FIA ES+ 241.8, ES− not observed).

Acetic acid 2-(4-bromo-5-methylpyrinin-2-ylamino)-butyl ester: 2-((S)-1-Hydroxymethylpropylamino)-5-methyl-4-nitro-pyridine N-oxide (146 mg, 0.61 mmol) was dissolved in acetyl bromide (1.5 mL). The mixture was then heated at 90° C. for 3 hours. The acteyl bromide was evaporated off under a stream of nitrogen and the crude material was dissolved in a solution of 2M $PCl_3$ in dichloromethane (2 mL). The resulting mixture was stirred at room temperature for 1 hour and the reaction mixture poured into an aqueous solution of saturated $NaHCO_3$ and extracted with ethyl acetate. The organic layer was washed with water, the solvent was then dried over $Na_2SO_4$ and removed under reduced pressure to afford the title compound as a brown oil (149 mg, ($R_t$(min) 4.146; FIA ES+ 300.9, ES− not observed).

4-[2-(S)-(1-Acetoxymethylpropylamino)-5-methylpyridin-4-yl]-1-(2,4,6-trime-thylbenzensulfonyl)-1H-pyrrole-2-carboxylic acid methyl ester: To a solution of acetic acid 2-(4-bromo-5-methylpyrinin-2-ylamino)-butyl ester (149 mg, 0.5 mmol, 1.0 equivalent) and 4-(4,4,5,5-tetramethyl-[1,3,2]dioxaborolan-2-yl)-1-(2,4,6-trimethylbenzensulfonyl)-1H-pyrrole-2-carboxylic acid methyl ester (215 mg, 0.50 mmol, 1.0 equivalent) in benzene (5 mL) was added aqueous 2M $Na_2CO_3$ (1 mL) and $Pd(PPh_3)_4$ (115.6 mg, 0.1 mmol, 0.2 equivalent). After heating at reflux for 16 hours, the mixture was poured in water and extracted with ethyl acetate. The organic extract was dried over $Na_2SO_4$ and the solvent removed under reduced pressure to afford the title compound ($R_t$(min) 6.684; FIA ES+ 528.3, ES− not observed) which was carried into the next step.

4-[2-(S)-Hydroxymethylpropylamino)-5-methylpyridin-4-yl]-1H-pyrrole-2-carboylic acid [1-(S)-(3-chlorophenylgylcinol]amide (1-3): The crude 4-[2-(S)-(1-acetoxymethylpropylamino)-5-methylpyridin-4-yl]-1-(2,4,6-trimethylbenzensulfonyl)-1H-pyrrole-2-carboxylic acid methyl ester was dissolved in methanol (1.5 mL) and aquous 1M, NaOH (2 mL) and the mixture heated at reflux for 16 hours. After acidifying with aqueous 1M HCl (2.2 mL), the solvent was removed under reduced pressure and the crude was then suspended in DMF (5 mL). After adding EDCI (192 mg, 1.0 mmol), HOBt (135 mg, 1.0 mmol) and DIEA (0.48 mL, 3.0 mmol), the mixture was stirred for 30 minutes at room temperature before adding. (S)-3-chlorophenylglycinol HCl salt (312 mg, 1.5 mmol) and the reaction mixture was then stirred for 16 hours at room temperature. The reaction mixture was dissolved in ethyl acetate, washed with water, the organic layer was dried over $Na_2SO_4$ and the solvent was removed under reduced pressure. The crude residue was purified by reversed phase HPLC (acetonitrile/water/TFA) to afford the title compound as a colorless solid (29.3 mg, 0.07 mmol, $R_t$(min) 4.563; FIA ES+ 443.1, ES− 441.5, ES+ 443.1, ES− 441.5; $^1$HNMR ($CD_3OD$) δ 1.0 (t, 3H), 1.50 (m, 1H), 1.7 (m, 1H), 2.3 (s, 3H), 3.5 (m, 1H), 3.7 (m, 2H), 3.8 (m, 2H), 5.1 (t, 1H), 7.0 (s, 1H), 7.3 (m, 4H), 7.4 (two s, 2H), 7.6 (s, 1H).

Example 4

Characterization Data

Compounds of the present invention were prepared by methods substantially similar to those described in the above Examples 1-3 and by methods known to one of ordinary skill in the art. The characterization data for these compounds is summarized in Table 3 below and includes HPLC, MS, and $^1$H NMR data. Unless specified otherwise, the $^1$NMR data was obtained at 500 MHz and all reported chemical shifts are ppm. Compound numbers correspond to the compound numbers listed in Tables 1, 2, and 3. As used herein, the term "$R_t$" refers to the retention time, in minutes, obtained for the designated compound using the HPLC method described above. Where more than one analytic measurement was obtained for any given compound, as described herein, only a single exemplary measurement is provided.

TABLE 3

Characterization Data for Selected Compounds of Formula I

| Cmpd # | M + 1 | $R_t$ | $^1$H NMR |
|---|---|---|---|
| I-1 | 413.00 | 2.10 | ($CD_3OD$)1.3(d, 6H), 2.3(s, 3H), 3.7(m, 3H), 5.1(t, 1H), 6.9(s, 1H), 7.2(m, 4H), 7.4(bs, 2H), 7.6(s, 1H) |
| I-2 | 379.20 | 2.00 | ($CD_3OD$)1.3(d, 6H), 2.3(s, 3H), 3.85(m, 3H), 5.15(t, 1H), 6.9 9s, 1H), 7.2(t, 1H), 7.3(m, 6H), 7.55(s, 1H) |
| I-3 | 443.10 | 2.10 | ($CD_3OD$)1.0(t, 3H), 1.5(m, 1H), 1.7(m, 1H), 2.3(s, 3H), 3.5(m, 1H), 3.7(m, 2H), 3.8(m, 2H), 5.1(t, 1H), 7.0(s, 1H), 7.3(m, 4H), 7.4(two s, 2H), 7.6(s, 1H) |
| I-4 | 393.30 | 2.10 | ($CD_3OD$)1.0(t, 3H), 1.3(d, 3H), 1.65(m, 2H), 2.35(s, 3H), 3.6(m, 1H), 3.8(m, 2H), 5.15(t, 1H), 6.95(s, 1H), 7.2(t, 1H), 7.3(t, 3H), 7.4(d, 1H), 7.45(s, 1H), 7.6(s, 1H) |
| I-5 | 427.20 | 2.40 | ($CD_3OD$)1.0(t, 3H), 1.2(d, 3H), 1.6(m, 2H), 2.3(s, 3H), 3.75(m, 1H), 3.85(m, 2H), 5.15(t, 1H), 6.95(s, 1H), 7.3(m, 4H), 7.5(two s, 2H), 7.6(s, 1H) |
| I-6 | 427.10 | 2.30 | ($CD_3OD$)0.9(, 3H), 1.25(d, 3H), 1.55(m, 2H), 2.25(s, 3H), 3.7(m, 1H), 3.85(m, 2H), 5.15(t, 1H), 6.6(s, 1H), 7.2(m, 4H), 7.5(s, 1H), 7.75(s, 1H) |
| I-7 | 427.10 | 2.40 | ($CD_3OD$)1.1(d, 6H), 1.9(m, 1H), 2.35(s, 3H), 3.15(d, 1H), 3.8(m, 2H), 5.2(m, 1H), 7.0(s, 1H), 7.3(m, 4H), 7.4(s, 1H), 7.6(s, 1H) |
| I-8 | 411.10 | 2.20 | ($CD_3OD$)0.65(m, 2H), 0.95(m, 2H), 2.4(s, 3H), 2.65(m, 1H), 3.8(m, 2H), 5.15(t, 1H), 7.0(s, 1H), 7.2(t, 1H), 7.3(m, 3H), 7.4(s, 1H), 7.45(s, 1H), 7.75(s, 1H) |
| I-9 | 433.70 | 2.30 | ($CD_3OD$)1.2(d, 6H), 3.8(m, 2H), 3.85(m, 1H), 5.1(t, 1H), 7.0(s, 1H), 7.2(m, 3H), 7.35(s, 1H), 7.4(7.65(s, 1H), 7.9(s, 1H) |
| I-10 | 399.90 | 2.10 | ($CD_3OD$)1.2(d, 6H), 3.8(d, 2H), 3.9(m, 1H), 5.1(t, 1H), 6.6(s, 1H), 7.2(t, 1H), 7.3(m, 5H), 7.45(s, 1H), 7.9(s, 1H) |
| I-11 | 415.10 | 1.90 | ($CD_3OD$)1.25(d, 3H), 3.5(m, 1H), 3.7(m, 1H), 3.8(m, 2H), 3.9(m, 1H), 5.2(t, 1H), 7.2(t, 1H), 7.3(t, 2H), 7.35(m, 2H), 7.45(s, 1H), 7.65(s, 1H), 7.9(s, 1H) |
| I-12 | 449.00 | 2.20 | ($CD_3OD$)1.2(d, 3H), 3.5(m, 1H), 3.7(m, 1H), 3.8(m, 2H), 3.9(m, 1H), 5.1(t, 1H), 7.1(s, 1H), 7.3(m, 3H), 7.4(s, 1H), 7.45(s, 1H), 7.7(s, 1H), 7.9(s, 1H) |
| I-13 | 462.90 | 2.20 | ($CD_3OD$)1.0(t, 3H), 1.6(m, 1H), 1.7(m, 1H), 3.55(m, 1H), 3.7(m, 2H), 3.8(m, 2H), 5.15(t, 1H), 7.1(s, 1H), 7.2(m, 3H), 7.4(s, 1H), 7.5(s, 1H), 7.7(s, 1H), 7.9(s, 1H) |

TABLE 3-continued

| Characterization Data for Selected Compounds of Formula I | | | |
|---|---|---|---|
| Cmpd # | M + 1 | $R_t$ | $^1$H NMR |
| I-14 | 429.00 | 2.00 | ($CD_3OD$)1.0(t, 3H), 1.55(m, 1H), 1.75(m, 1H), 3.5(m, 1H), 3.7(m, 2H), 3.8(m, 2H), 5.1(t, 1H), 7.1(s, 1H), 7.2(d, 1H), 7.3(t, 2H), 7.35(m, 2H), 7.4(s, 1H), 7.7(s, 1H), 7.9(s, 1H) |
| I-15 | 447.10 | 2.50 | ($CD_3OD$)1.0(t, 2H), 1.3(d, 3H), 1.7(m, 2H), 3.7(m, 1H), 3.85(m, 2H), 5.15(t, 1H), 7.1(s, 1H), 7.25(m, 3H), 7.4(s, 1H), 7.5(s, 1H), 7.7(s, 1H) |
| I-16 | 477.00 | 2.40 | ($CD_3OD$)1.0(t, 3H), 1.6(m, 1H), 1.8(m, 1H), 3.6(m, 1H), 3.7(m, 2H), 3.85(m, 2H), 3.9(s, 3H), 5.1(t, 1H), 7.1(s, 1H), 7.25(m, 1H), 7.3(m, 2H), 7.4(2s, 2H), 7.7(s, 1H), 7.95(s, 1H) |
| I-17 | 433.00 | 2.30 | ($CD_3OD$): 8.0(s, 1H), 7.7(s, 1H), 7.25-7.5(m, 6H), 5.15(m, 1H), 3.8-3.95(m, 3H), 1.3(d, 6H) |
| I-18 | 449.00 | 2.36 | ($CD_3OD$)7.96(s, 1H); 7.7(s, 1H); 7.48(s, 1H); 7.42(s, 1H); 7.32(s, 2H); 7.24(s, 2H); 7.2(s, 1H); 5.15(t, 1H); 3.8-4.0(m. 5H); 3.72(m, 1H); 3.57(m, 1H); 1.3(s, 3H) |

Example 5

Synthesis of Prodrugs

Prodrugs of formula II are prepared from the hydroxyl compounds of formula I by a variety of methods known to one of ordinary skill in the art. These methods include, but are not limited to, acylation by a desired carboxylic acid or phosphate formation. When the hydroxyl moiety of formula I is acylated by a desired amino acid, the amino moiety of the amino acid may be optionally protected by a suitable amino protecting group as described herein supra.

The preparation of the L-valine prodrug of compound I-9 is described in detail below.

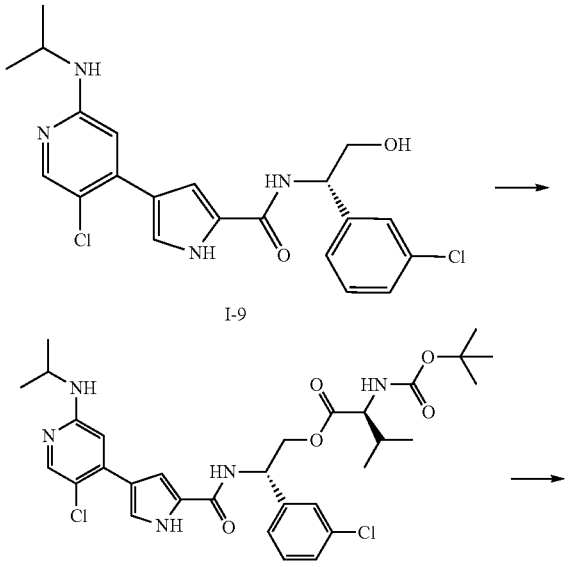

I-9

-continued

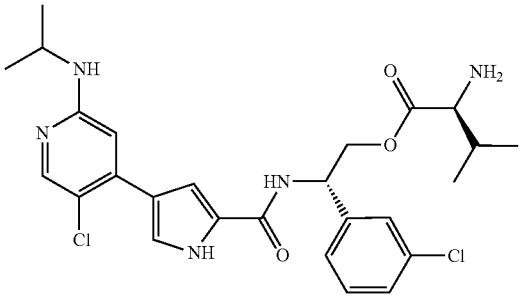

II-1

(2S)-(S)-2-(4-(5-chloro-2-(isopropylamino)pyridine-4-yl)-1H-pyrrole-2-carboxamido)-2-(3-chlorophenyl)ethyl-2-amino-2-methylbutanoate (II-1): To a solution of compound 1-9 (1 g, 2.3 mmol, 1.0 equivalent) in dichloromethane (50 mL) were added DIEA (1.1 mL, 6.9 mmol, 3.0 equivalent) and N—BOC-L-Valine (1.2 g, 5.52 mmol, 2.4 equivalents). PyBOP (2.9 g, 5.75 mmol, 2.5 equivalents.) was then added slowly and the resulting mixture was stirred at room temperature for 48 hours. The mixture was then washed with water and dried over sodium sulfate. The crude solid was adsorbed on silica and then purified by flash chromatography eluting with mixtures of hexane/ethyl acetate (from 90:10 to 50:50), yielding the Boc-protected compound as a white solid (786 mg). This intermediate (761 mg, 1.2 mmol) was dissolved in dioxane (1 mL) and treated with a solution of 4 M HCL in dioxane. The resulting mixture was stirred for 16 hours at room temperature. The solvent was then removed and the 2×HCl salt of the title compound was obtained as a white solid (571 mg). HPLC $R_t$: 4.56 minutes. FIA MS: 531.9 ES+; 529.8 ES−. LC/MS: $R_t$: 2.07 minutes; 532.0 ES+; 530.1 ES−. $^1$HNMR ($CD_3OD$) δ 0.9 (dd, 6H), 1.35 (d, 6H), 2.2 (m, 1H), 3.9 (m, 2H), 4.7 (m, 2H), 5.6 (m, 1H), 7.1 (s, 1H), 7.3 (d, 1H), 7.35 (t, 1H), 7.4 (d, 1H), 7.5 (s, 1H), 7.6 (s, 1H), 7.75 (s, 1H), 7.95 (s, 1H).

The preparation of a phosphate prodrug of compound 1-9 is described in detail below.

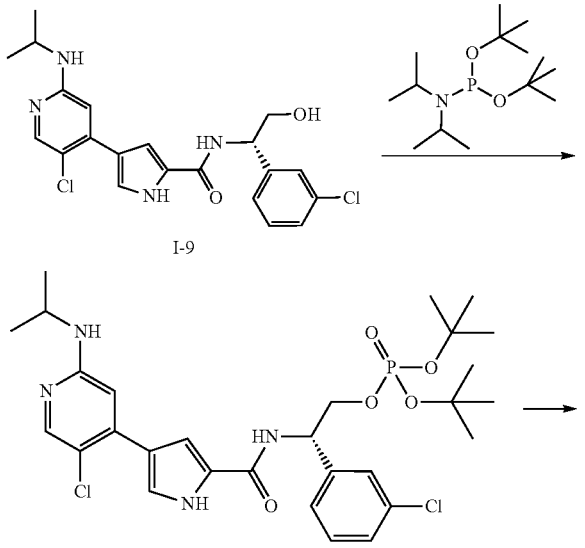

I-9

-continued

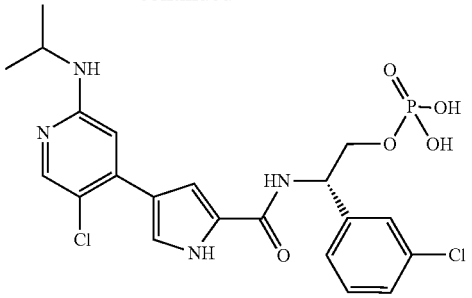

II-2 di-tert-Butyl 4-(5-chloro-2-(isopropylamino)pyridine-4-yl)-N-((S)-1-(3-chlorophenyl)-2-hydroxyethyl)-1H-pyrrole-2-carboxamide phosphate: Compound 1-9 (1 g, 2.3 mmol, 1.0 equivalent) and tetrazole (241 mg, 3.45 mmol, 1.5 equivalents) were dissolved in dichloromethane (5 mL) and acetonitrile (5 mL) under nitrogen at room temperature. Di-tert-butyl diisopropyl phosphoamidite (1.1 mL, 3.45 mmol, 1.5 equivalents) was added dropwise and the resulting mixture was stirred for 16 hours. The reaction mixture was then cooled on an ice bath, treated with a solution of 6 M tert-butylhydroxyperoxide (3 mL) and stirred for 20 minutes. The clear solution was diluted in dichloromethane and small amount of methanol, washed with $Na_2S_2O_3$, water and dried over sodium sulfate. The crude oil was adsorbed on silica gel and was first purified by flash chromatography eluting with mixtures of hexane/acetone (from 90:10 to 60:40) and then by reversed phase HPLC (acetonitrile/water/1% TFA), yielding the di-t-butyl ether intermediate as a white solid (336 mg). HPLC $R_t$: 6.53 minutes, MS FIA: 625.0 ES+; 623.1 ES−.

4-(5-Chloro-2-(isopropylamino)pyridine-4-yl)-N-((S)-1-(3-chlorophenyl)-2-hydroxyethyl)-1H-pyrrole-2-carboxamide phosphate (II-2): The t-butyl phosphate intermediate (336 mg, 0.54 mmol) was suspended in dioxane (5 mL) and a solution of 4 M HCL in dioxane was added. The resulting mixture was stirred at room temperature for 1 hour. The solvent was then removed and the free phosphate was then dissolved in a solution of DMSO (15 mL), methanol (50 mL) and water (25 mL) and treated with a solution of 2 M $Na_2CO_3$ (0.25 mL). Methanol was removed under reduced pressure and the aqueous/DMSO mixture was remove using a liophilizer to afford the title compound as an off white solid (187 mg). HPLC $R_t$: 4.24 minutes. FIA MS: 512.9 ES+; 510.9 ES−. LC/MS: $R_t$ 2.39 minutes; 512.9 ES+; 510.9 ES−. $^1$HNMR ($CD_3OD$) δ 1.2 (d, 6H), 3.9 (m, 1H), 4.1 (dm, 2H), 5.1 (m, 1H), 6.7 (s, 1H), 7.2 (d, 1H), 7.25 (t, 1H), 7.3 (m, 2H), 7.45 (s, 1H), 7.55 (s, 1H), 7.9 (s, 1H).

Example 6

ERK2 Inhibition Assay

Compounds were assayed for the inhibition of ERK2 by a spectrophotometric coupled-enzyme assay (Fox et al (1998) Protein Sci 7, 2249). In this assay, a fixed concentration of activated ERK2 (10 nM) was incubated with various concentrations of the compound in DMSO (2.5%) for 10 minutes at 30° C. in 0.1 M HEPES buffer, pH 7.5, comtaining 10 mM, $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $IC_{50}$ was evaluated from the rate data as a function of inhibitor concentration.

Compounds of the present invention we found to be inhibitors of ERK2 protein kinase. In certain embodiments, compounds were found to inhibit ERK2 kinase at <0.1 μM. In other embodiments, compounds were found to inhibit ERK2 kinase at <0.01 μM.

Example 7

ERK1 Inhibition Assay

Compounds are assayed for the inhibition of ERK1 by a spectrophotometric coupled-enzyme assay (Fox et al (1998) Protein Sci 7, 2249). In this assay, a fixed concentration of activated ERK1 (20 nM) is incubated with various concentrations of the compound in DMSO (2.0%) for 10 minutes at 30° C. in 0.1 M HEPES buffer, pH 7.6, containing 10 mM $MgCl_2$, 2.5 mM phosphoenolpyruvate, 200 μM NADH, 30 μg/mL pyruvate kinase, 10 μg/mL lactate dehydrogenase, and 150 μM erktide peptide. The reaction is initiated by the addition of 140 μM ATP (20 μL). The rate of decrease of absorbance at 340 nM is monitored. The $K_i$ is evaluated from the rate data as a function of inhibitor concentration.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

[1. A compound of formula I:

I

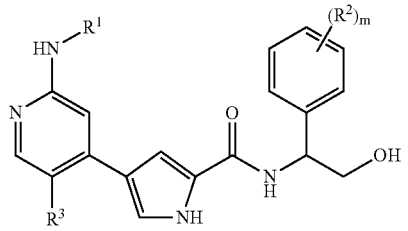

or a pharmaceutically acceptable salt thereof, wherein:

$R^1$ is a $C_{1-6}$ aliphatic group, wherein $R^1$ is optionally substituted with up to 2 groups independently selected from —OR or —$C_{1-3}$ haloalkyl;

each R is independently hydrogen or $C_{1-4}$ aliphatic;

$R^2$ is R, fluoro, or chloro;

m is 0, 1, or 2; and $R^3$ is hydrogen, $C_{1-3}$ aliphatic, fluoro, or chloro; wherein each aliphatic group is, independently, a saturated or unsaturated straight or branched hydrocarbon chain or monocyclic non-aromatic hydrocarbon.]

[2. The compound according to claim 1, wherein $R^1$ is $C_{1-4}$ aliphatic optionally substituted with —OR or —$C_{1-3}$ haloalkyl.]

[3. The compound according to claim 2, wherein $R^1$ is $C_{1-4}$ aliphatic optionally substituted with —OH, —$CHF_2$, —$CH_2F$, or —$CF_3$.]

[4. The compound according to claim 3, wherein $R^1$ is isopropyl, 2-butyl, cyclopropyl, or ethyl, wherein each moiety is optionally substituted with —OH or —$CF_3$.]

[5. The compound according to claim 1, wherein $R^2$ is hydrogen, $C_{1-3}$ aliphatic, or chloro.]
[6. The compound according to claim 1, wherein $R^3$ is hydrogen, methyl, or chloro.]
[7. A compound selected from the group consisting of:
I-1
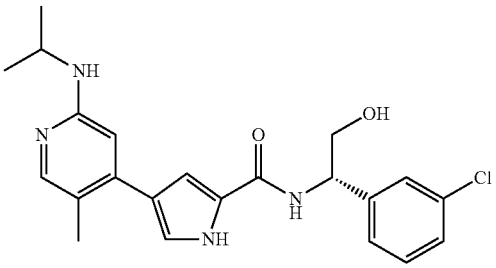
I-2
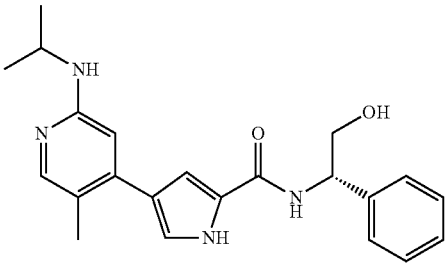
I-3
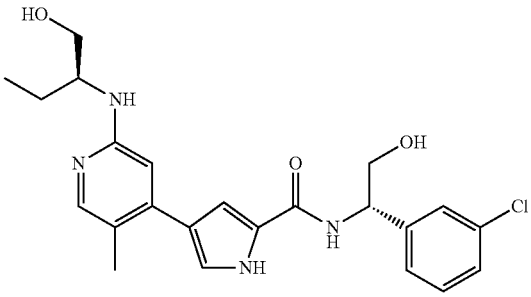
I-4
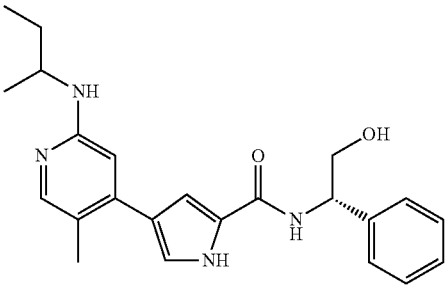
I-5
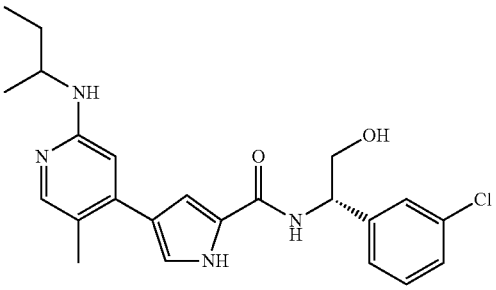
-continued
I-6
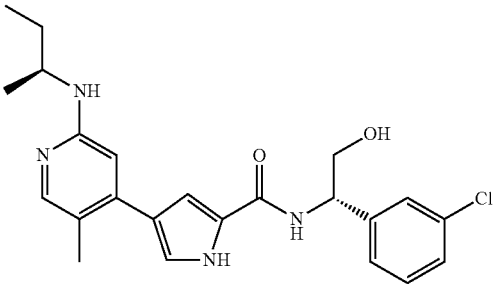
I-7
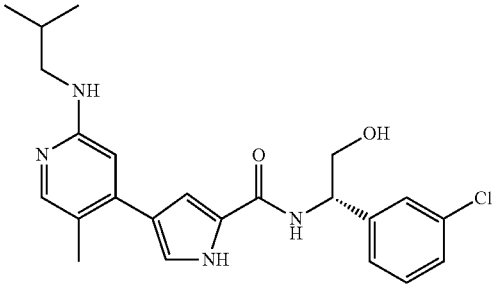
I-8
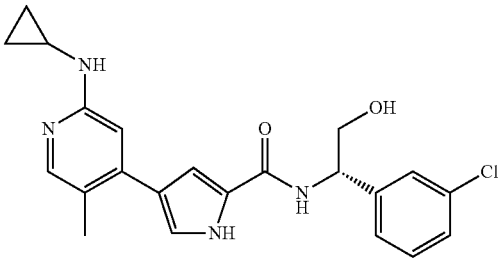
I-9
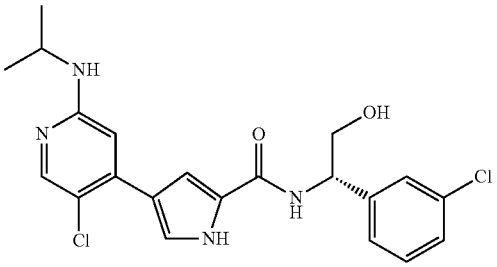
I-10
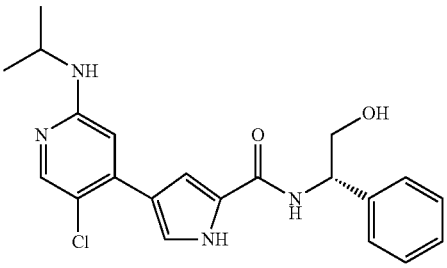

-continued

I-11

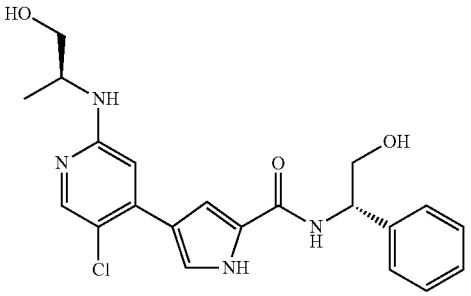

I-12

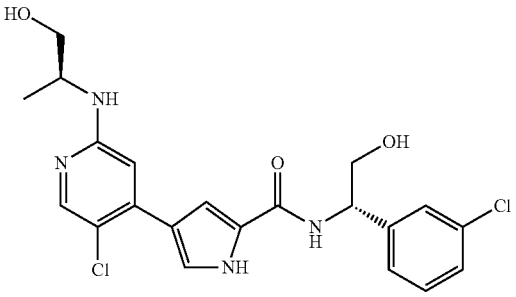

I-13

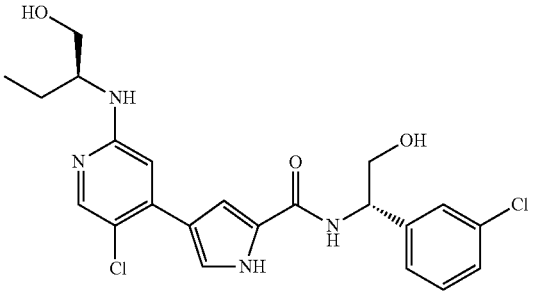

I-14

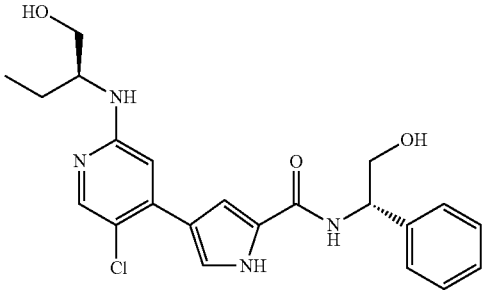

I-15

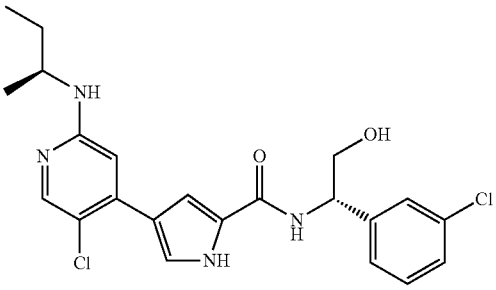

-continued

I-16

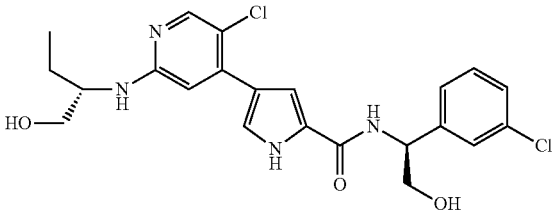

I-17

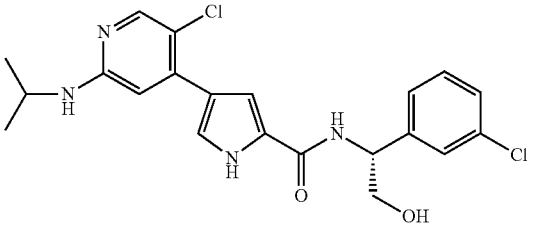

and

I-18

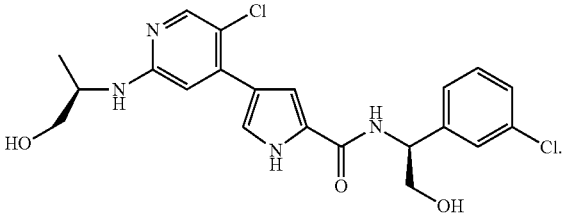

]

[8. A composition comprising a compound according to claim 1 and a pharmaceutically acceptable carrier, adjuvant, or vehicle.]

[9. The compound according to claim 1, wherein:

$R^1$ is isopropyl or 2-butyl, wherein $R^1$ is optionally substituted with one —OH;

$R^2$ is H or Cl;

m is 1; and $R^3$ is Cl or methyl.]

*10. The compound*

*I-6*

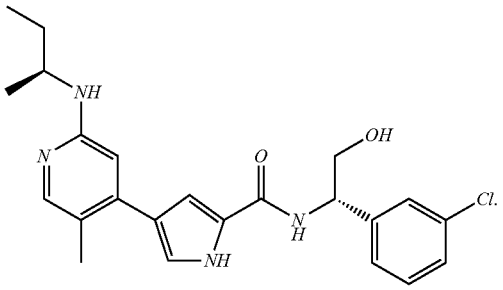

*11. A composition comprising a compound according to claim 10 and a pharmaceutically acceptable carrier, adjuvant, or vehicle.*

12. The compound

I-13

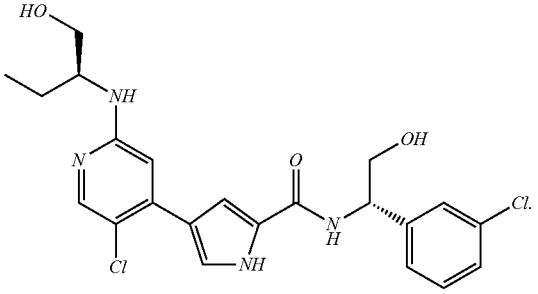

13. A composition comprising a compound according to claim 12 and a pharmaceutically acceptable carrier, adjuvant, or vehicle.

14. A pharmaceutically acceptable salt of the compound

I-6

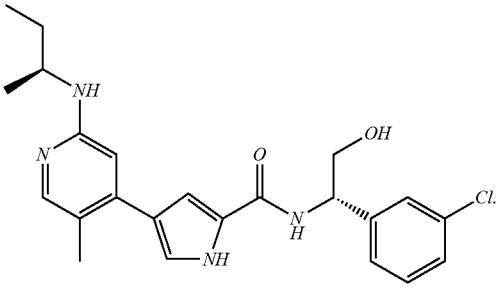

15. A composition comprising the pharmaceutically acceptable salt of the compound according to claim 14 and a pharmaceutically acceptable carrier, adjuvant, or vehicle.

16. A pharmaceutically acceptable salt of the compound

I-13

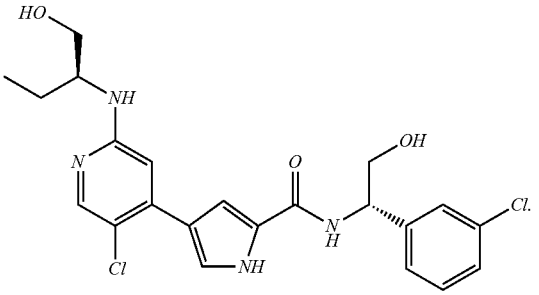

17. A composition comprising the pharmaceutically acceptable salt of the compound according to claim 16 and a pharmaceutically acceptable carrier, adjuvant, or vehicle.

* * * * *